(12) United States Patent
Scarisbrick

(10) Patent No.: US 9,669,094 B2
(45) Date of Patent: Jun. 6, 2017

(54) METHODS FOR INCREASING SUSCEPTIBILITY TO APOPTOSIS BY ADMINISTERING AN INHIBITOR OF KALLIKREIN 6 POLYPEPTIDE ACTIVITY

(71) Applicant: Mayo Foundation for Medical Education and Research, Rochester, MN (US)

(72) Inventor: Isobel A. Scarisbrick, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 149 days.

(21) Appl. No.: 13/962,686

(22) Filed: Aug. 8, 2013

(65) Prior Publication Data
US 2013/0315926 A1    Nov. 28, 2013

Related U.S. Application Data

(62) Division of application No. 13/250,599, filed on Sep. 30, 2011, now Pat. No. 8,530,427.

(60) Provisional application No. 61/388,289, filed on Sep. 30, 2010.

(51) Int. Cl.
| | | |
|---|---|---|
| *A61K 39/395* | (2006.01) |
| *A61K 31/7088* | (2006.01) |
| *A61K 31/7105* | (2006.01) |
| *A61K 38/48* | (2006.01) |
| *C12N 9/64* | (2006.01) |
| *A61K 31/713* | (2006.01) |

(52) U.S. Cl.
CPC .... *A61K 39/39558* (2013.01); *A61K 31/7088* (2013.01); *A61K 31/713* (2013.01); *A61K 31/7105* (2013.01); *A61K 38/4853* (2013.01); *C12N 9/6445* (2013.01); *C12Y 304/21008* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,816,567 A | 3/1989 | Cabilly et al. |

(Continued)

FOREIGN PATENT DOCUMENTS

WO    2005/078117    8/2005

OTHER PUBLICATIONS

Lou et al., Correlation beween KLK6 expression and clinicopathological features of glioma, Contemp. Oncol. 18(4):246-251, Aug. 2014.*

(Continued)

*Primary Examiner* — Claire Kaufman
(74) *Attorney, Agent, or Firm* — Fish & Richardson P.C.

(57) ABSTRACT

This document provides methods and materials involved in modulating a cell's ability to be resistant to apoptosis. For example, methods and materials for exposing cells to KLK6 polypeptides, or increased KLK6 polypeptide activity, to promote resistance to apoptosis are provided. In addition, methods and materials for reducing the ability of KLK6 polypeptides to promote resistance to apoptosis are provided.

4 Claims, 23 Drawing Sheets

(56) References Cited

U.S. PATENT DOCUMENTS

| | | |
|---|---|---|
| 5,214,136 A | 5/1993 | Lin et al. |
| 5,218,105 A | 6/1993 | Cook et al. |
| 5,235,033 A | 8/1993 | Summerton et al. |
| 5,482,856 A | 1/1996 | Fell, Jr. et al. |
| 5,565,332 A | 10/1996 | Hoogenboom et al. |
| 5,596,086 A | 1/1997 | Matteucci et al. |
| 5,750,666 A | 5/1998 | Caruthers et al. |
| 6,054,297 A | 4/2000 | Carter et al. |
| 6,808,901 B1 | 10/2004 | Neuberger et al. |
| 6,933,146 B2 | 8/2005 | Helliwell et al. |
| 8,530,427 B2 | 9/2013 | Scarisbrick |
| 2004/0096443 A1 | 5/2004 | Traynelis et al. |
| 2011/0065676 A1 | 3/2011 | Perelman et al. |
| 2016/0000791 A1 | 1/2016 | Scarisbrick |

OTHER PUBLICATIONS

Sotiropoulou et al., Abstract 4916: Molecular basis for the concentration-dependent tumor suppressing effects of KLK6 in breast cancer, Canc. Res. 72(8), Supp. 1, Abstract No. 4916, Apr. 2012.*

Su et al.,Inhibitory effect of KLK7 siRNA on gastric cancer AGS cell lines, Chinese J. Canc. Biother. 20(2):207-211, 2013 (Chinese with English abstract).*

Y.A. Hannun, Apoptosis and the delimma of cancer chemotherapy, Blood, 89(6):1845-1853, Mar. 15, 1997.*

Drucker et al., Clinical significance and novel mechanism of action of kallikrein 6 in glioblastoma, Neuro-Oncol. 15(3):305-318, 2013.*

Kupferman et al., Molecular analysis of anoikis resistance in oral cavity squamous cell carcinoma. Oral Oncol. (May 2007) vol. 43, No. 5, pp. 440-454. Electronic Publication Date: Sep. 15, 2006.*

Loessner et al., Combined expression of KLK4, KLK5, KLK6, and KLK7 by ovarian cancer cells leads to decreased adhesion and paclitaxel-induced chemoresistance, Gynecol. Oncol. 127:569-578, 2012.*

Weich et al., Differential gene expression in non-human primate bone marrow following irradiation and administration of carboplatin, Blood, 98(11)pt.1, p. 551a, Nov. 16, 2001.*

Bernett et al., Crystal structure and biochemical characterization of human kallikrein 6 reveals that a trypsin-like kallikrein is expressed in the central nervous system, J. Biol. Chem. 277(27):24562, Jul. 5, 2002.

Blaber et al., "Enzymatic Properties of Rat Myelencephalon-Specific Protease," *Biochem.*, 2002, 41:1165-1173.

Blaber et al., "Targeting kallikrein 6 proteolysis attenuates CNS inflammatory disease," *FASEB J.*, 2004, 18:920-922.

Borgono et al., "Human Tissue Kallikreins: Physiologic Roles and Applications in Cancer," *Mol. Cancer Res.*, 2004, 2:257-280.

Chow et al., "Kallikreins is microRNA targets: an in silico and experimental-based analysis," *Biological Chem.*, Jun. 2008, 389:731-738.

Christophi et al., "Distinct promoters regulate tissue-specific and differential expression of kallikrein 6 in CNS demyelinating disease," *J. Neurochem.*, 2004, 91:1439-1449.

Cole et al., "Monoclonal Antibodies and Cancer Therapy," Alan R. Liss Inc., 1983, pp. 77-96.

Cote et al., "Generation of human monoclonal antibodies reactive with cellular antigens," *PNAS*, 1983, 80:2026-2030.

Database GenBank, Accession No. NM_002774,*Homo sapiens* kallikrein-related peptidase 6 (KLK6), transcript variant A, mRNA, Nov. 4, 2012, accessed Dec. 11, 2012.

Diamandis et al., "Human kallikrein 6 (zyme/protease M/neurosin): a new serum biomarker of ovarian carcinoma," *Clin. Biochem.*, 2000, 33:579-583.

Ed. Ausubel, *Short Protocols in Molecular Biology*, Chapter 11, Green Publishing Associates and John Wiley & Sons, ed. 1992, 56 pages.

Ed. Machida *Viral Vectors for Gene Therapy: Methods and Protocols*, Humana Press, 2003, 6 pages (Table of Contents Only).

Ed. Morgan, *Gene Therapy Protocols (Methods in Molecular Medicine)*, Humana Press, 2002, 3 pages (Table of Contents Only).

Eischen et al., "Comparison of Apoptosis in Wild-Type and Fas-Resistant Cells: Chemotherapy-Induced Apoptosis is not dependent on Fas/Fas Ligand Interactions," *Blood*, 1997, 90:935-943.

GenBank Accession No. AF013988, May 2008, 2 pages, accessed Mar. 14, 2013.

GenBank Accession No. AF016239, Sep. 1999, 2 pages, accessed Mar. 14, 2013.

GenBank Accession No. AF149289, Jun. 2000, 4 pages, accessed Mar. 14, 2013.

GenBank Accession No. D78203, Feb. 1999, 2 pages, accessed Mar. 14, 2013.

GenBank Accession No. NM_019175.1, 2013, accessed Mar. 14, 2013.

GenBank Database [online], *Homo sapiens* kallikrein 1 (KLK1), mRNA, Accession NM 002257, Apr. 17, 2013 [retrieved on May 9, 2013].

Henkaus et al., "Kallikrein 6 is a mediator of K-RAS-dependent migration of colon carcinoma cells," *Biological Chem.*, 2008, 389:757-764.

Huse et al., "Generation of a Large Combinatorial Library of the Immunoglobulin Repertoire in Phage Lambda," *Science*, Dec. 1989, 246:1275.

Hyrup et al., "Peptide Nucleic Acids (PNA): Synthesis, Properties and Potential Applications," *Bioorgan. Med. Chem.*, 1996, 4:5-23.

Klucky et al., Kallikrein 6 induces e-cadherin shedding and promotes cell proliferation, migration, and invasion, Cancer Res. 67:8198-8206, Sep. 2007.

Kohler et al., "Continuous cultures of fused cells secreting antibody of predefined specificity," *Nature*, 1975, 256:495.

Kozbor and Roder, "The production of monoclonal antibodies from human lymphocytes," *Immunology Today*, 1983, 4:72.

Laxmikanthan et al., "1.70 Å X-Ray Structure of Human *apo* Kallikrein 1: Structural Changes Upon Peptide Inhibitor/Substrate Binding," *Proteins*, 2005, 58:802-814.

NCI Drug Dictionary, National Cancer Institute, arsenic trioxide [online], [retrieved Dec. 11, 2012] Retrieved from the internet <URL:http://www.cancergov/drugdictionary?CdrID=43067>.

Pampalakis et al., Tissue kallikrein proteolytic cascade pathways in normal physiology and cancer, Biochem. Biophys. Acta, 1776:22-31, 2007.

Scarisbrick et al., "Activity of a newly identified serine protease in CNS demyelination," *Brain*, 2002, 125:1283-1296.

Scarisbrick et al., Kallikreins are associated with secondary progressive multiple sclerosis and promote neurodegeneration, *Biological Chem.*, 2008, 389:739-745.

Scarisbrick et al., "Potential scope of action of tissue kallikreins in CNS immune-mediated disease," *J. Neuroimmunology*, 2006, 178:167-176.

Summerton and Weller, "Morpholino Antisense Oligomers: Design, Preparation, and Properties," *Antisense Nucleic Acid Drug Dev.*, 1997, 7:187-195.

Vandell et al., "Protease-activated receptor dependent and independent signaling by kallikreins 1 and 6 in CNS neuron and astroglial cell lines," *J. Neurochem.*, 2008, 107:855-870.

Wang et al., "Direct gene delivery of human tissue kallikrein reduces blood pressure in spontaneously hypertensive rats," *J. Clin. Invest.* 95:1710-1716, Apr. 1995.

Xia et al., Kallikrein protects against ischemic stroke by inhibiting apoptosis and inflammation and promoting angiogenesis and neurogenesis, *Human Gene Ther.* 17:206-219, Feb. 2006.

Zarghooni et al., "Decreased concentration of human kallikrein 6 in brain extracts of Alzheimer's disease patients," *Clin. Biochem.*, 2002, 35:225-231.

Adams et al., "Structure, function and pathophysiology of protease activated receptors," *Pharmacol Ther.*, 130(3):248-282, Epub Jan. 26, 2011.

Angelo et al., "Substrate specificity of human kallikrein 6: salt and glycosaminoglycan activation effects," *J Biol Chem.*, 281(6):3116-3126, Epub Dec. 1, 2005.

(56) References Cited

OTHER PUBLICATIONS

Arai et al., "Thrombin and prothrombin are expressed by neurons and glial cells and accumulate in neurofibrillary tangles in Alzheimer disease brain," *J Neuropathol Exp Neurol.*, 65(1):19-25, Jan. 2006.
Back et al., "Maturation-dependent vulnerability of oligodendrocytes to oxidative stress-induced death caused by glutathione depletion," *J Neurosci.*, 18(16):6241-6253, Aug. 15, 1998.
Boven et al., "Up-regulation of proteinase-activated receptor 1 expression in astrocytes during HIV encephalitis," *J Immunol.*, 170(5):2638-2646, Mar. 1, 2003.
Burda et al., "Critical role for PAR1 in kallikrein 6-mediated oligodendrogliopathy," *Glia.*, 61(9):1456-1470, Epub Jul. 8, 2013.
Burda et al., "Hormone-like activity of kallikrein 6 regulates oligodendrocyte differentiation and white matter degeneration," [presentation abstract] 42nd Annual Society for Neuroscience meeting, New Orleans, LA, 2 pages, 2012.
Cahoy et al., "A transcriptome database for astrocytes, neurons, and oligodendrocytes: a new resource for understanding brain development and function," *J Neurosci.*, 28(1):264-278, Jan. 2, 2008.
Chang et al., "Premyelinating oligodendrocytes in chronic lesions of multiple sclerosis," *N Engl J Med.*, 346(3):165-173, Jan. 17, 2002.
Chen et al., "Thrombin activity associated with neuronal damage during acute focal ischemia," *J Neurosci.*, 32(22):7622-7631, May 30, 2012.
Citron et al., "Upregulation of neurotoxic serine proteases, prothrombin, and protease-activated receptor 1 early after spinal cord injury," *J Neurotrauma.*, 17(12):1191-1203, Dec. 2000.
Cogoni and Masino, "Gene silencing in Neurospora crassa requires a protein homologous to RNA-dependent RNA polymerase," *Nature.*, 399(6732):166-169, May 13, 1999.
Cogoni et al., "Transgene silencing of the al-1 gene in vegetative cells of Neurospora is mediated by a cytoplasmic effector and does not depend on DNA-DNA interactions or DNA methylation," *EMBO J.*, 15(12):3153-3163, Jun. 17, 1996.
Crawford et al., "Remyelination: the true regeneration of the central nervous system," *J Comp Pathol.*, 149(2-3):242-254, Epub Jul. 5, 2013.
Cristiano et al., "Molecular conjugates: a targeted gene delivery vector for molecular medicine," *J Mol Med (Berl).*, 73(10):479-486, Oct. 1995.
Czopka et al., "Regulatory mechanisms that mediate tenascin C-dependent inhibition of oligodendrocyte precursor differentiation," *J Neurosci.*, 30(37):12310-12322, Sep. 15, 2010.
Dell'Albani et al., "Oligodendroglial survival factors, PDGF-AA and CNTF, activate similar JAK/STAT signaling pathways," *J Neurosci Res.*, 54(2):191-205, Oct. 15, 1998.
Denic et al., "Brainstem 1H nuclear magnetic resonance (NMR) spectroscopy: marker of demyelination and repair in spinal cord," *Ann Neurol.*, 66(4):559-564, Oct. 2009.
Fancy et al., "Myelin regeneration: a recapitulation of development?" *Annu Rev Neurosci.*, 34:21-43, 2011.
Fern et al., "Rapid ischemic cell death in immature oligodendrocytes: a fatal glutamate release feedback loop," *J Neurosci.*, 20(1):34-42, Jan. 1, 2000.
Fire et al., "Potent and specific genetic interference by double-stranded RNA in Caenorhabditis elegans," *Nature*, 391(6669):806-811, Feb. 19, 1998.
Franklin, "Why does remyelination fail in multiple sclerosis?" *Nat Rev Neurosci.*, 3(9):705-714, Sep. 2002.
Friedmann et al., "T cell-mediated neuroprotection involves antithrombin activity," *J Neuroimmunol.*, 121(1-2):12-21, Dec. 3, 2001.
Funfschilling et al., "Glycolytic oligodendrocytes maintain myelin and long-term axonal integrity," *Nature*, 485(7399):517-521, Apr. 29, 2012.
Fyffe-Maricich et al., "Signaling through ERK1/2 controls myelin thickness during myelin repair in the adult central nervous system," *J Neurosci.*, 33(47):18402-18408, Nov. 20, 2013.
Fyffe-Maricich et al., "The ERK2 mitogen-activated protein kinase regulates the timing of oligodendrocyte differentiation," *J Neurosci.*, 31(3):843-850, Jan. 19, 2011.
Gingrich et al., "Serine proteases and brain damage—is there a link?" *Trends Neurosci.*, 23(9):399-407, Sep. 2000.
Guardiola-Diaz et al., "Erk1/2 MAPK and mTOR signaling sequentially regulates progression through distinct stages of oligodendrocyte differentiation," *Glia.*, 60(3):476-486, Epub Dec. 5, 2011.
Hamill et al., "Protease-activated receptor 1-dependent neuronal damage involves NMDA receptor function," *Exp Neurol.*, 217(1):136-146, Epub Feb. 10, 2009.
Han et al., "Activation of protease activated receptor 1 increases the excitability of the dentate granule neurons of hippocampus," *Mol Brain.*, 4:32, Aug. 10, 2011.
Han et al., "Proteomic analysis of active multiple sclerosis lesions reveals therapeutic targets," *Nature*, 451(7182):1076-1081, Epub Feb. 17, 2008.
Harrington et al., "Oligodendrocyte PTEN is required for myelin and axonal integrity, not remyelination," *Ann Neurol.*, 68(5):703-716, Nov. 2010.
Huang et al., "Retinoid X receptor gamma signaling accelerates CNS remyelination," *Nat Neurosci.*, 14(1):45-53, Epub Dec. 5, 2010.
Ishii et al., "ERK1/ERK2 MAPK signaling is required to increase myelin thickness independent of oligodendrocyte differentiation and initiation of myelination," *J Neurosci.*, 32(26):8855-8864, Jun. 27, 2012.
Ishii et al., "Sustained activation of ERK1/2 MAPK in oligodendrocytes and schwann cells enhances myelin growth and stimulates oligodendrocyte progenitor expansion," *J Neurosci.*, 33(1):175-186, Jan. 2, 2013.
Juliet et al., "Toxic effect of blood components on perinatal rat subventricular zone cells and oligodendrocyte precursor cell proliferation, differentiation and migration in culture," *J Neurochem.*, 109(5):1285-1299, Epub Mar. 25, 2009.
Jung et al., "Lines of murine oligodendroglial precursor cells immortalized by an activated neu tyrosine kinase show distinct degrees of interaction with axons in vitro and in vivo," *Eur J Neurosci.*, 7(6):1245-1265, Jun. 1, 1995.
Junge et al., "Protease-activated receptor-1 in human brain: localization and functional expression in astrocytes," *Exp Neurol.*, 188(1):94-103, Jul. 2004.
Keirstead et al., "Identification of post-mitotic oligodendrocytes incapable of remyelination within the demyelinated adult spinal cord," *J Neuropathol Exp Neurol.*, 56(11):1191-1201, Nov. 1997.
Kennerdell and Carthew, "Use of dsRNA-mediated genetic interference to demonstrate that frizzled and frizzled 2 act in the wingless pathway," *Cell.*, 95(7):1017-1026, Dec. 23, 1998.
Kremer et al., "The complex world of oligodendroglial differentiation inhibitors," *Ann Neurol.*, 69(4):602-618, Apr. 2011.
Kuhlmann et al., "Differentiation block of oligodendroglial progenitor cells as a cause for remyelination failure in chronic multiple sclerosis," *Brain*, 131(Pt 7):1749-1758, Epub May 30, 2008.
Ligon et al., "Olig gene function in CNS development and disease," *Glia.*, 54(1):1-10, Jul. 2006.
Lundwall et al., "A comprehensive nomenclature for serine proteases with homology to tissue kallikreins," *Biol Chem.*, 387(6):637-641, Jun. 2006.
Luo et al., "Protease-activated receptors in the brain: receptor expression, activation, and functions in neurodegeneration and neuroprotection," *Brain Res Rev.*, 56(2):331-345, Epub Aug. 29, 2007.
Matute et al., "P2X(7) receptor blockade prevents ATP excitotoxicity in oligodendrocytes and ameliorates experimental autoimmune encephalomyelitis," *J Neurosci.*, 27(35):9525-9533, Aug. 29, 2007.
McCarthy and de Vellis, "Preparation of separate astroglial and oligodendroglial cell cultures from rat cerebral tissue," *J Cell Biol.*, 85(3):890-902, Jun. 1980.
Mifsud et al., "Oligodendrocyte pathophysiology and treatment strategies in cerebral ischemia," *CNS Neurosci Ther.*, 20(7):603-612, Epub Apr. 7, 2014.

(56) References Cited

OTHER PUBLICATIONS

Misquitta and Paterson, "Targeted disruption of gene function in *Drosophila* by RNA interference (RNA-i): a role for nautilus in embryonic somatic muscle formation," *Proc Natl Acad Sci U S A.*, 96(4): 1451-1456, Feb. 16, 1999.
Nicole et al., "Activation of protease-activated receptor-1 triggers astrogliosis after brain injury," *J Neurosci.*, 25(17):4319-4329, Apr. 27, 2005.
Nobuta et al., "STAT3-mediated astrogliosis protects myelin development in neonatal brain injury," *Ann Neurol.*, 72(5):750-765, Epub Aug. 31, 2012.
Oikonomopoulou et al., "Proteinase-activated receptors, targets for kallikrein signaling," *J Biol Chem.*, 281(43):32095-32112, Epub Aug. 2, 2006.
Oikonomopoulou et al., "Proteinase-mediated cell signalling: targeting proteinase-activated receptors (PARs) by kallikreins and more," *Biol Chem.*, 387(6):677-685, Jun. 2006.
Oldstone et al., "Virus-induced alterations in homeostasis: alterations in differentiated functions of infected cells in vivo," *Science*, 218(4577):1125-1127, Dec. 10, 1982.
Olson et al., "PAR-1 deficiency protects against neuronal damage and neurologic deficits after unilateral cerebral hypoxia/ischemia," *J Cereb Blood Flow Metab.*, 24(9):964-971, Sep. 2004.
Riek-Burchardt et al., "Increase of prothrombin-mRNA after global cerebral ischemia in rats, with constant expression of protease nexin-1 and protease-activated receptors," *Neurosci Lett.*, 329(2):181-184, Aug. 30, 2002.
Romano and Masino, "Quelling: transient inactivation of gene expression in Neurospora crassa by transformation with homologous sequences," *Mol Microbiol.*, 6(22):3343-3353, Nov. 1992.
Scarisbrick et al., "Dynamic role of kallikrein 6 in traumatic spinal cord injury," *Eur J Neurosci.*, 24(5):1457-1469, Sep. 2006.
Scarisbrick et al., "Functional role of kallikrein 6 in regulating immune cell survival," *PLoS One.*, 6(3):e18376, Mar. 28, 2011.
Scarisbrick et al., "Kallikrein 6 is a novel molecular trigger of reactive astrogliosis," *Biol Chem.*, 393(5):355-367, Apr. 2012.
Scarisbrick et al., "Kallikrein 6 regulates early CNS demyelination in a viral model of multiple sclerosis," *Brain Pathol.*, 22(5):709-722, Epub Mar. 21, 2012.
Scarisbrick et al., "MSP, a trypsin-like serine protease, is abundantly expressed in the human nervous system," *J Comp Neurol.*, 431(3):347-361, Mar. 12, 2001.
Scarisbrick et al., "Nervous system-specific expression of a novel serine protease: regulation in the adult rat spinal cord by excitotoxic injury," *J Neurosci.*, 17(21):8156-8168, Nov. 1, 1997.
Scarisbrick et al., "Preferential expression of myelencephalon-specific protease by oligodendrocytes of the adult rat spinal cord white matter," *Glia.*, 30(3):219-230, May 2000.
Striggow et al., "The protease thrombin is an endogenous mediator of hippocampal neuroprotection against ischemia at low concentrations but causes degeneration at high concentrations," *Proc Natl Acad Sci U S A.*, 97(5):2264-2269, Feb. 29, 2000.
Suo et al., "Participation of protease-activated receptor-1 in thrombin-induced microglial activation," *J Neurochem.*, 80(4):655-666, Feb. 2002.
Tripathi et al., "Prominent oligodendrocyte genesis along the border of spinal contusion lesions," *Glia.*, 55(7):698-711, May 2007.
Volpe et al., "The developing oligodendrocyte: key cellular target in brain injury in the premature infant," *Int J Dev Neurosci.*, 29(4):423-440, Epub Mar. 5, 2011.
Vu et al., "Domains specifying thrombin-receptor interaction," *Nature*, 353(6345):674-677, Oct. 17, 1991.
Wang et al., "Expression of protease-activated receptors (PARs) in OLN-93 oligodendroglial cells and mechanism of PAR-1-induced calcium signaling," *Neuroscience.*, 126(1):69-82, 2004.
Wang et al., "Four subtypes of protease-activated receptors, co-expressed in rat astrocytes, evoke different physiological signaling," *Glia.*, 37(1):53-63, Jan. 2002.
Wang et al., "P2X7 receptor inhibition improves recovery after spinal cord injury," *Nat Med.*, 10(8):821-827, Epub Jul. 18, 2004.
Wilson and Brophy, "Role for the oligodendrocyte cytoskeleton in myelination," *J Neurosci Res.*, 22(4):439-448, Apr. 1989.
Wolswijk et al., "Chronic stage multiple sclerosis lesions contain a relatively quiescent population of oligodendrocyte precursor cells," *J Neurosci.*, 18(2):601-609, Jan. 15, 1998.
Wrathall et al., "Myelin gene expression after experimental contusive spinal cord injury," *J Neurosci.*, 18(21):8780-8793, Nov. 1, 1998.
Yoon et al., "Kallikrein 6 signals through PAR1 and PAR2 to promote neuron injury and exacerbate glutamate neurotoxicity," *J Neurochem.*, 127(2):283-298, Epub May 27, 2013.
Yoon et al., "The thrombin receptor is a critical extracellular switch controlling myelination," *Glia*, 63(5):846-859, Epub Jan. 27, 2015.
Yousef and Diamandis, "The new human tissue kallikrein gene family: structure, function, and association to disease," *Endocr Rev.*, 22(2):184-204, Apr. 2001.

\* cited by examiner

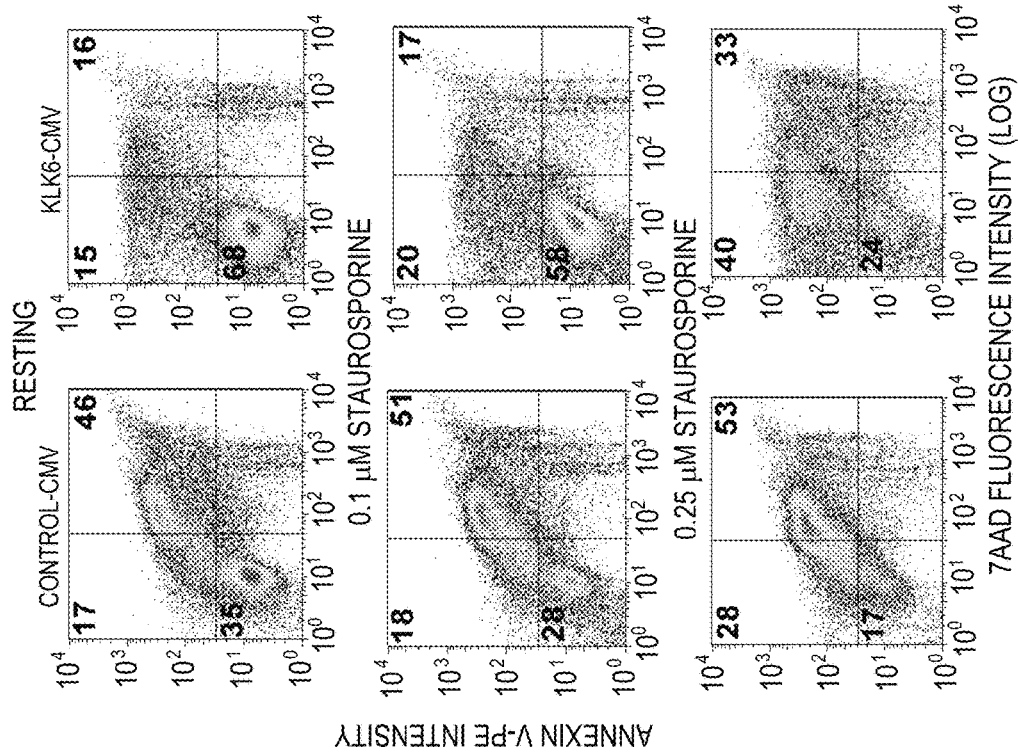
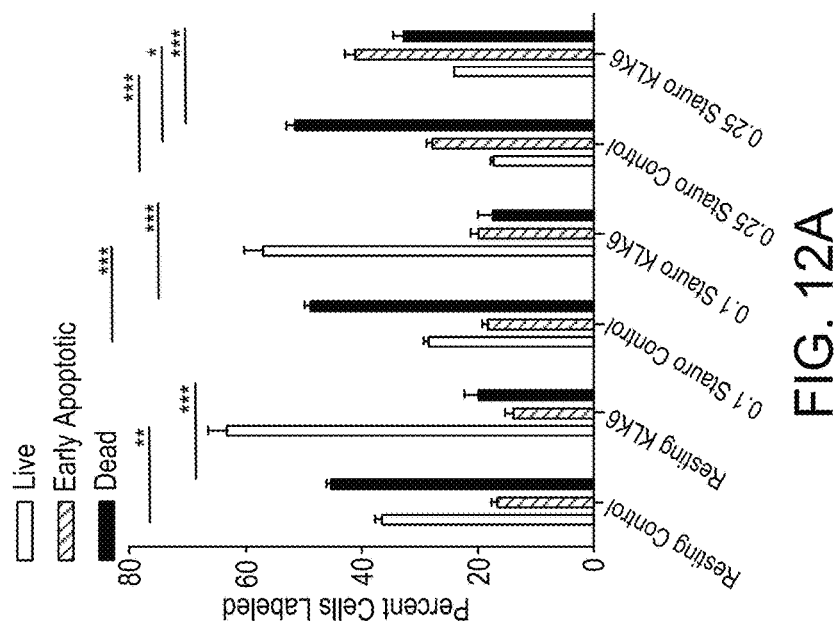
FIG. 12A
FIG. 12B

```
   1 ggcggacaaa gcccgattgt tcctgggccc tttccccatc gcgcctgggc ctgctccca
  61 gcccggggca ggggcggggg ccagtgtggt gacacacgct gtagctgtct ccccggctgg
 121 ctggctcgct ctctcctggg gacacagagg tcggcaggca gcacacagag ggacctacgg
 181 gcagctgttc cttcccccga ctcaagaatc cccggaggcc cggaggcctg cagcaggagc
 241 ggccatgaag aagctgatgg tggtgctgag tctgattgct gcagcctggg cagaggagca
 301 gaataagttg gtgcatggcg gaccctgcga caagacatct caccoctacc aagctgccct
 361 ctacacctcg ggccacttgc tctgtggtgg ggtccttatc catccactgt gggtcctcac
 421 agctgcccac tgcaaaaaac cgaatcttca ggtcttcctg gggaagcata accttcggca
 481 aagggagagt tccaggagc agagttctgt tgtccgggct gtgatccacc ctgactatga
 541 tgccgccagc catgaccagg acatcatgct gttgcgcctg gcacgcccag ccaaactctc
 601 tgaactcatc cagccccttc cctggagag ggactgctca gccaacacca ccagctgcca
 661 catcctgggc tggggcaaga cagcagatgg tgatttccct gacaccatcc agtgtgcata
 721 catccacctg gtgtcccgtg aggagtgtga gcatgcctac cctggccaga tcacccagaa
 781 catgttgtgt gctggggatg agaagtacgg gaaggattcc tgccagggtg attctggggg
 841 tccgctggta tgtggagacc acctccgagg ccttgtgtca tggggtaaca tccctgtgg
 901 atcaaaggag aagccaggag tctacaccaa cgtctgcaga tacacgaact ggatccaaaa
 961 aaccattcag gccaagtgac cctgacatgt gacatctacc tcccgaccta ccaccccact
1021 ggctggttcc agaacgtctc tcacctagac cttgcctccc ctcctctcct gcccagctct
1081 gaccctgatg cttaataaac gcagcgacgt gagggtcctg attctccctg gttttacccc
1141 agctccatcc ttgcatcact ggggaggacg tgatgagtga ggacttgggt cctcggtctt
1201 accccacca ctaagagaat acaggaaaat cccttctagg catctcctct ccccaaccct
1261 tccacgtt tgatttcttc ctgcagaggc ccagccacgt gtctggaatc ccagctccgc
1321 tgcttactgt cggtgtcccc ttgggatgta cctttcttca ctgcagattt ctcacctgta
1381 agatgaagat aaggatgata cagtctccat aaggcagtgg ctgttggaaa gatttaaggt
1441 ttcacaccta tgacatacat ggaatagcac ctgggccacc atgcactcaa taaagaatga
1501 attttattat gaaaaaaaaa aaaaaa   (SEQ ID NO:1)
```

MKKLMVVLSLIAAAWAEEQNKLVHGGPCDKTSHPYQAALYTSGHLLCGGVLIHPLWVLTAAHCK
KPNLQVFLGKHNLRQRESSQEQSSVVRAVIHPDYDAASHDQDIMLLRLARPAKLSELIQPLPLE
RDCSANTTSCHILGWGKTADGDFPDTIQCAYIHLVSREECEHAYPGQITQNMLCAGDEKYGKDS
CQGDSGGPLVCGDHLRGLVSWGNIPCGSKEKPGVYTNVCRYTNWIQKTIQAK  (SEQ ID NO:2)

SEQUENCE LISTING

<160> NUMBER OF SEQ ID NOS: 6

<210> SEQ ID NO 1
<211> LENGTH: 1527
<212> TYPE: DNA
<213> ORGANISM: Homo sapiens

<400> SEQUENCE: 1
ggcggacaaa gcccgattgt tcctgggccc tttccccatc gcgcctgggc ctgctcccca    60

```
gcccggggca ggggcggggg ccagtgtggt gacacacgct gtagctgtct ccccggctgg    120
ctggctcgct ctctcctggg gacacagagg tcggcaggca gcacacagag ggacctacgg    180
gcagctgttc cttcccccga ctcaagaatc cccggaggcc cggaggcctg cagcaggagc    240
ggccatgaag aagctgatgg tggtgctgag tctgattgct gcagcctggg cagaggagca    300
gaataagttg gtgcatggcg gaccctgcga caagacatct caccccctac aagctgccct    360
ctacacctcg ggccacttgc tctgtggtgg ggtccttatc catccactgt gggtcctcac    420
agctgcccac tgcaaaaaac cgaatcttca ggtcttcctg ggaagcata accttcggca    480 aagggagagt tccaggagc agagttctgt tgtccgggct gtgatccacc ctgactatga    540
tgccgccagc catgaccagg acatcatgct gttgcgcctg cacgcccag ccaaactctc    600 tgaactcatc cagcccctc ccctggagag ggactgctca gccaacacca ccagctgcca    660
catcctgggc tggggcaaga cagcagatgg tgatttccct gacaccatcc agtgtgcata    720
catccacctg gtgtcccgtg aggagtgtga gcatgcctac cctggccaga tcacccagaa    780
catgttgtgt gctggggatg agaagtacgg gaaggattcc tgccagggtg attctggggg    840
tccgctggta tgtggagacc acctccgagg ccttgtgtca tggggtaaca tcccctgtgg    900
atcaaaggag aagccaggag tctacaccaa cgtctgcaga tacacgaact ggatccaaaa    960
aaccattcag gccaagtgac cctgacatgt gacatctacc tcccgaccta ccaccccact   1020
ggctggttcc agaacgtctc tcacctagac cttgcctccc ctcctctcct gcccagctct   1080
gaccctgatg cttaataaac gcagcgacgt gagggtcctg attctccctg gttttacccc   1140
agctccatcc ttgcatcact ggggaggacg tgatgagtga ggacttgggt cctcggtctt   1200
acccccacca ctaagagaat acaggaaaat cccttctagg catctcctct ccccaaccct   1260
tccacacgtt tgatttcttc ctgcagaggc ccagccacgt gtctggaatc ccagctccgc   1320
tgcttactgt cggtgtcccc ttgggatgta ccttcttca ctgcagattt ctcacctgta   1380
agatgaagat aaggatgata cagtctccat aaggcagtgg ctgttggaaa gatttaaggt   1440
ttcacaccta tgcatacat ggaatagcac ctgggccacc atgcactcaa taaagaatga   1500
attttattat gaaaaaaaaa aaaaaaa                                       1527

<210> SEQ ID NO 2
<211> LENGTH: 244
<212> TYPE: PRT
<213> ORGANISM: Homo sapiens

<400> SEQUENCE: 2

Met Lys Lys Leu Met Val Val Leu Ser Leu Ile Ala Ala Ala Trp Ala
 1               5                  10                  15

Glu Glu Gln Asn Lys Leu Val His Gly Gly Pro Cys Asp Lys Thr Ser
            20                  25                  30

His Pro Tyr Gln Ala Ala Leu Tyr Thr Ser Gly His Leu Leu Cys Gly
        35                  40                  45

Gly Val Leu Ile His Pro Leu Trp Val Leu Thr Ala Ala His Cys Lys
    50                  55                  60

Lys Pro Asn Leu Gln Val Phe Leu Gly Lys His Asn Leu Arg Gln Arg
65                  70                  75                  80

Glu Ser Ser Gln Glu Gln Ser Ser Val Val Arg Ala Val Ile His Pro
                85                  90                  95

Asp Tyr Asp Ala Ala Ser His Asp Gln Asp Ile Met Leu Leu Arg Leu
            100                 105                 110
```

```
Ala Arg Pro Ala Lys Leu Ser Glu Leu Ile Gln Pro Leu Pro Leu Glu
    115                 120                 125

Arg Asp Cys Ser Ala Asn Thr Thr Ser Cys His Ile Leu Gly Trp Gly
130                 135                 140

Lys Thr Ala Asp Gly Asp Phe Pro Asp Thr Ile Gln Cys Ala Tyr Ile
145                 150                 155                 160

His Leu Val Ser Arg Glu Glu Cys Glu His Ala Tyr Pro Gly Gln Ile
                165                 170                 175

Thr Gln Asn Met Leu Cys Ala Gly Asp Glu Lys Tyr Gly Lys Asp Ser
            180                 185                 190

Cys Gln Gly Asp Ser Gly Gly Pro Leu Val Cys Gly Asp His Leu Arg
        195                 200                 205

Gly Leu Val Ser Trp Gly Asn Ile Pro Cys Gly Ser Lys Glu Lys Pro
    210                 215                 220

Gly Val Tyr Thr Asn Val Cys Arg Tyr Thr Asn Trp Ile Gln Lys Thr
225                 230                 235                 240

Ile Gln Ala Lys

<210> SEQ ID NO 3
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 3
gagcagaata agttggtgca t                                          21

<210> SEQ ID NO 4
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 4
cctctacacc tcgggccact t                                          21

<210> SEQ ID NO 5
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 5
agccaaactc tctgaactca t                                          21

<210> SEQ ID NO 6
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 6
gatgagaagt acgggaagga t                                          21
```

METHODS FOR INCREASING SUSCEPTIBILITY TO APOPTOSIS BY ADMINISTERING AN INHIBITOR OF KALLIKREIN 6 POLYPEPTIDE ACTIVITY

CROSS-REFERENCE TO RELATED APPLICATIONS

This application is a divisional of U.S. application Ser. No. 13/250,599, filed Sep. 30, 2011, which claims the benefit of U.S. Provisional Application Ser. No. 61/388,289, filed Sep. 30, 2010.

STATEMENT AS TO FEDERALLY SPONSORED RESEARCH

This invention was made with government support under grant number NS052741 awarded by the National Institutes of Health. The government has certain rights in the invention.

BACKGROUND

1. Technical Field

This document relates to methods and materials involved in modulating a cell's ability to be resistant to apoptosis. For example, this document relates to methods and materials for using, for example, kallikrein 6 polypeptides to promote resistance to apoptosis. This document also relates to methods and materials for using, for example, kallikrein 6 polypeptide inhibitors to reduce resistance to apoptosis.

2. Background Information

Kallikrein 6 (KLK6) polypeptides are members of the kallikrein gene family that includes secreted serine proteases aligned on human chromosome 19q13.3-4. These gene family members form the largest contiguous cluster of serine proteases in the human genome.

SUMMARY

This document provides methods and materials involved in modulating a cell's ability to be resistant to apoptosis. For example, this document provides methods and materials for exposing cells to KLK6 polypeptides, or increased KLK6 polypeptide activity, to promote resistance to apoptosis. As described herein, the exposure of wide range of different cells to KLK6 polypeptides promotes the survival of those cells under resting conditions and/or under conditions that normally promote apoptosis. For example, lymphocytes, monocytes, oligodendrocytes, astrocytes, and glioma cells normally undergo measurable apoptosis upon treatment with an apoptosis-inducing agent (e.g., camptothecin, ConA, or staurosporine). Treatment with KLK6 polypeptides, however, promotes cell survival of cells exposed to an apoptosis-inducing agent, thereby reducing the apoptosis-inducing effects of the apoptosis-inducing agent. As described herein, KLK6 polypeptides, molecules designed to increase KLK6 polypeptide expression levels, and molecules designed to increase KLK6 polypeptide activity can be used to treat conditions that exhibit undesirable apoptosis. For example, conditions and diseases that involve too much cell death can be treated using KLK6 polypeptides, molecules designed to increase KLK6 polypeptide expression levels, or molecules designed to increase KLK6 polypeptide activity. Having the ability to increase survival of cells that may undergo apoptosis can allow clinicians and other health care professionals to reduce the effects and symptoms associated with, for example, excessive apoptosis.

This document also provides methods and materials for reducing the ability of KLK6 polypeptides to promote resistance to apoptosis. For example, an inhibitor of KLK6 polypeptide activity can be used to reduce KLK6 polypeptide-induced resistance to apoptosis. As described herein, KLK6 polypeptide inhibitors and molecules designed to reduce KLK6 polypeptide expression can be used to treat conditions and diseases that exhibit undesirable resistance to apoptosis. Having the ability to reduce the resistance to apoptosis can allow clinicians and other health care professionals to reduce the effects and symptoms associated with, for example, cells exhibiting excessive resistance to apoptosis.

One advantage of using KLK6 polypeptides as a therapeutic target to regulate cell survival/death is that this polypeptide is a secreted enzyme that acts in the extracellular space, thereby eliminating the need for intracellular targeting strategies. Another advantage of using KLK6 polypeptides as a therapeutic target is that KLK6 polypeptides appear to have broad physiological relevance to a wide range of cell types and clinical disorders.

In general, one aspect of this document features a method for treating a mammal having a condition wherein cells undergo excessive apoptosis. The method comprises, or consists essentially of, administering a composition comprising, or consists essentially of, a KLK6 polypeptide or a nucleic acid encoding said KLK6 polypeptide to the mammal under conditions wherein the composition reduces the level of apoptosis of the cells. The composition can comprise, or consist essentially of, the KLK6 polypeptide. The composition can comprise, or consist essentially of, the nucleic acid encoding the KLK6 polypeptide. The mammal can be a human. The condition can be a condition resulting from the withdrawal of growth factors or the activation of cell surface death receptors. The condition can be a condition resulting from exposure to heat shock, hypoxia, UV radiation, dexamethasone, cytotoxic agents, or chemotherapeutic agents.

In another aspect, this document features a method for treating a mammal having cancer. The method comprises, or consists essentially of, administering a composition comprising, or consisting essentially of, an inhibitor of a KLK6 polypeptide expression or activity to the mammal under conditions wherein the composition increases the level of apoptosis of cancer cells within the mammal. The composition can comprise, or consist essentially of, a KLK6 antisense molecule or a KLK6 miRNA molecule. The composition can comprise, or consist essentially of, an anti-KLK6 polypeptide antibody. The mammal can be a human.

In another aspect, this document features a method for treating a mammal having an inflammatory condition. The method comprises, or consists essentially of, administering a composition comprising, or consisting essentially of, an inhibitor of a KLK6 polypeptide expression or activity to the mammal under conditions wherein the composition increases the level of apoptosis of cells within the mammal. In some cases, the method can include monitoring the level of apoptosis within the mammal. The composition can comprise, or consist essentially of, a KLK6 antisense molecule or a KLK6 miRNA molecule. The composition can comprise, or consist essentially of, an anti-KLK6 polypeptide antibody. The mammal can be a human.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A contains graphs demonstrating that stimulation of cultures with either 1 or 10 µg/mL of KLK6 polypeptides, but not KLK1 polypeptides, significantly reduced the number of dead (PI+) cells observed at either the 24- or 72-hour time points. FIG. 1B is a graph plotting the results obtained as 72 hours. FIG. 1C contains graphs plotting the intensity of CFSE labeling in PI– cells determined using the proliferation platform of the Flow Jo Program and labeling peaks observed after 24 hours. FIG. 1D contains a graph demonstrating that KLK1 polypeptides (10 µg/ml), but not KLK6 polypeptides, promoted a significant increase in the percent of cells divided at the 24-hour time point. Data are expressed as mean+SEM, One Way ANOVA with SNK post hoc test; $P<0.001**$, $P<0.02*$; (SSC, side scatter).

FIG. 2A contains a graph plotting results for total cell death. FIG. 2B contains a graph plotting results for T cell death. FIG. 2C contains a graph plotting results for B cell death.

FIG. 3A contains a graph plotting results for total cell death. FIG. 3B contains a graph plotting results for T cell death. FIG. 3C contains a graph plotting results for B cell death.

FIG. 6A is a graph demonstrating that KLK6 polypeptides significantly reduced the number of dead cells (Annexin V+ and PI+) observed in cultures of splenocytes under resting conditions and after exposure to dexamethasone (0.1 µM) or staurosporine (1 µM). Reduced cell death was accompanied by a significant increase in the live population (unlabeled cells) in the case of cells under resting conditions and those exposed to staurosporine. KLK6 polypeptides also promoted an accumulation of splenocytes at early apoptotic stages (Annexin V+, PI–) in the presence of apoptosis inducing agents, suggesting KLK6 polypeptides delay the apoptotic cascade. Data are expressed as mean+ SEM; One Way ANOVA with SNK post hoc test for multiple comparisons, $P<0.001*$, $P<0.003$, $P<0.007*$.

FIG. 7A is a graph demonstrating that the absence of PAR1 blocked the ability of KLK6 polypeptides to rescue CD3+ T cells from death under resting conditions but in the presence of dexamethasone (0.1 µM) any effect of PAR1 deletion did not reach the level of statistical significance. FIG. 7B is a graph demonstrating that PAR1 deficiency also blocked the ability of KLK6 polypeptides to rescue B220+ B cells from resting cell death and significantly reduced KLK6 polypeptide-mediated B cell rescue in the presence of dexamethasone. FIG. 7C is a graph demonstrating that neither PAR1- or PAR2-APs alone, or in combination with PAR4-AP (FIG. 7D), were able to mimic the pro-survival effects of KLK6 polypeptides. PAR1-AP alone in the presence of dexamethasone exacerbated cell death. Data are expressed as mean+SEM; two-way comparisons A and B, made using Students t-test, $P<0.003$*, $P<0.009$, $P=0.03$; One Way ANOVA with SNK post hoc test for multiple comparisons in FIGS. 7C and D, $P<0.001$*, $P<0.002$; $P<0.012$*.

FIGS. 12A-B contain a graph (A) and flow cytometry results (B) demonstrating that KLK6 over expression in Jurkat leukemia T cells reduces cell death. Jurkat T cells were stably transduced with a vector in which the human KLK6 gene is constitutively expressed under the control of a CMV promoter, or with an empty vector (Control), and levels of live (Annexin V-PE− and 7AAD−), early apoptotic (Annexin V-PE+ and 7AAD−), or dead (Annexin V-PE+ and 7AAD+) cells were determined by flow cytometry under resting conditions, or after 24 hour periods of exposure to 0.1 or 0.25 µM staurosporine. (FIG. 12A) Histogram and corresponding dot plots (FIG. 12B), demonstrate KLK6 over expression produces effects largely parallel to those afforded by treatment of cultures with recombinant KLK6. There was a decrease in the percentage of dead cells and an increase in the number of live cells in Jurkat T cells over expressing KLK6, relative to those expressing an empty vector. KLK6 over expression also reduced cell death in the presence of 0.1 or 0.25 µM staurosporine relative to that seen in cells stably transduced with empty vector. Reductions in cell death were likely to reflect in part a delay in apoptosis, since after 24 hour exposure to 0.25 µM Staurosporine, KLK6 over expression not only reduced the number of dead cells and increased the number of live cells, but cells in the early stages of apoptosis (AnnV-PE+, 7AAD−) were also significantly elevated. Data are expressed as mean+SEM of triplicate cultures examined in parallel; One Way ANOVA with SNK post hoc test for multiple comparisons, $P<0.001$*, $P=0.002$, $P=0.003$*. All data shown is representative of that seen in at least three independent cell culture experiments.

(FIG. 17A) Shows flow cytometry dot blots of the U251 GBM cell line transfected with a control CMV driven construct alone or a vector containing a KLK6-CMV driven construct. Dead cells were detected by labeling with 7-AAD. FIG. 17B is a histogram showing a quantitative analysis of triplicate samples demonstrating cells transfected with the KLK6 expressing vector (KLK6-CMV) exhibited significantly reduced cell death in the presence of 1 µM staurosporine. FIG. 17C contains quantitative real time PCR results showing that cells transfected with the KLK6-CMV construct express significantly higher levels of KLK6 mRNA. All expression data were normalized to the constitutively expressed gene GAPDH (*P<0.05, Students t-test).

(FIG. 20B) Cell death in response to 24 hour exposure to Cisplatin (2.5 µg/mL) was also measured by flow cytometry using PI to label dead cells. As revealed by the clonogenicity assay, U251 GBM cells over expressing KLK6 (KLK6-CMV) were more resistant to 24 hour exposure to Cisplatin than were cells expressing an empty control vector. Histogram represents triplicate samples assessed by flow cytometry (*P<0.05, Students t-test).

FIGS. 22A-B contain a listing of a nucleic acid sequence (FIG. 22A) and an amino acid sequence (FIG. 22B) of a human KLK6 polypeptide. The amino acid sequence of a mature active KLK6 polypeptide is underlined.

DETAILED DESCRIPTION

Figure 1A:
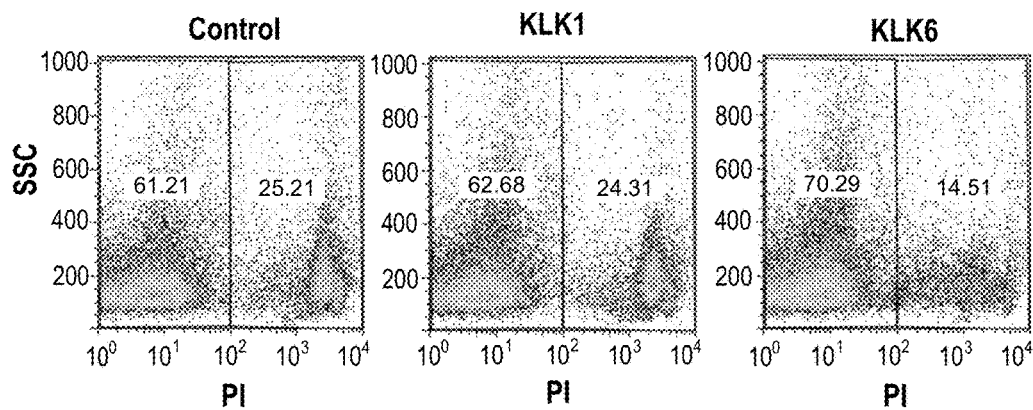
FIGS. 1A-D contain graphs demonstrating the differential effects of KLK1 and KLK6 polypeptides on survival and proliferation of murine splenocytes. Murine splenocytes were labeled with CFSE (carboxyfluorescein succinimidyl ester) and cultured in defined media in the presence of 1 or 10 µg/mL of KLK1 or KLK6 polypeptides, or vehicle alone (control), for periods of 24 or 72 hours. At harvest, dead cells were labeled using PI (propidium iodide), and samples were examined by flow cytometry.
Figure 1B:
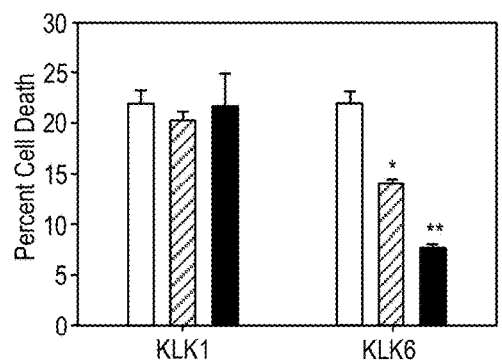
Figure 1D:
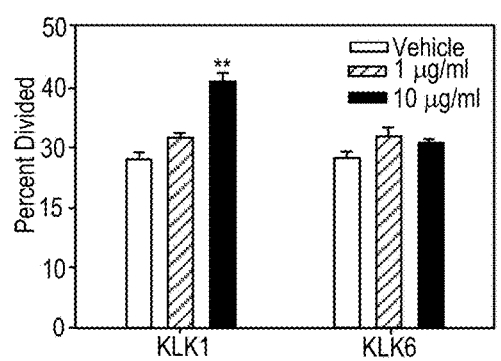
Figure 1C:
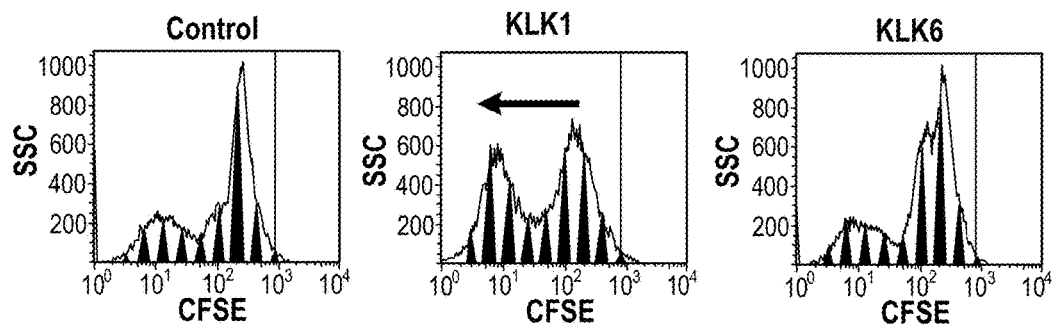
Figure 2:
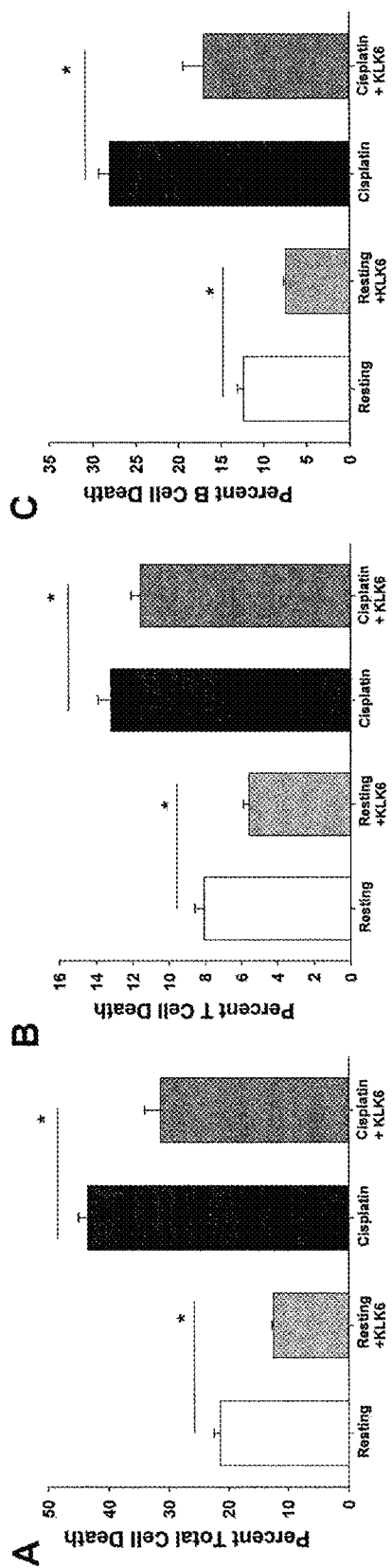
FIGS. 2A-C contain graphs demonstrating that KLK6 blocks cisplatin induced lymphocyte death. Recombinant KLK6 blocks death of murine T and B cells under resting conditions and in the presence of 25 µg/mL of the chemotherapeutic cisplatin ($*P<0.05$, Students t-test). Percent cell death was determined by quantification of propidium iodide labeled cells using flow cytometry. Results from 24 hour exposure times are shown.
Figure 3:
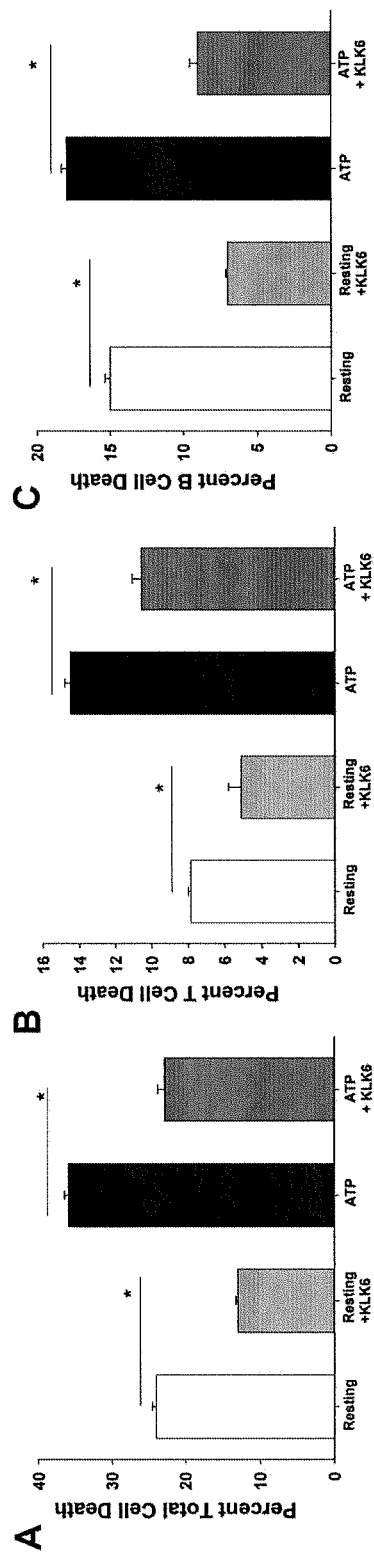
FIGS. 3A-C contain graphs demonstrating that KLK6 blocks ATP induced lymphocyte death. Recombinant KLK6 blocks death of murine T and B cells under resting conditions and in the presence of 100 µM ATP, which is known to trigger calcium influx and apoptosis ($*P<0.05$, Students t-test). Percent cell death was determined by quantification of propidium iodide labeled cells using flow cytometry. Results from 24 hour exposure times are shown.
Figure 4:
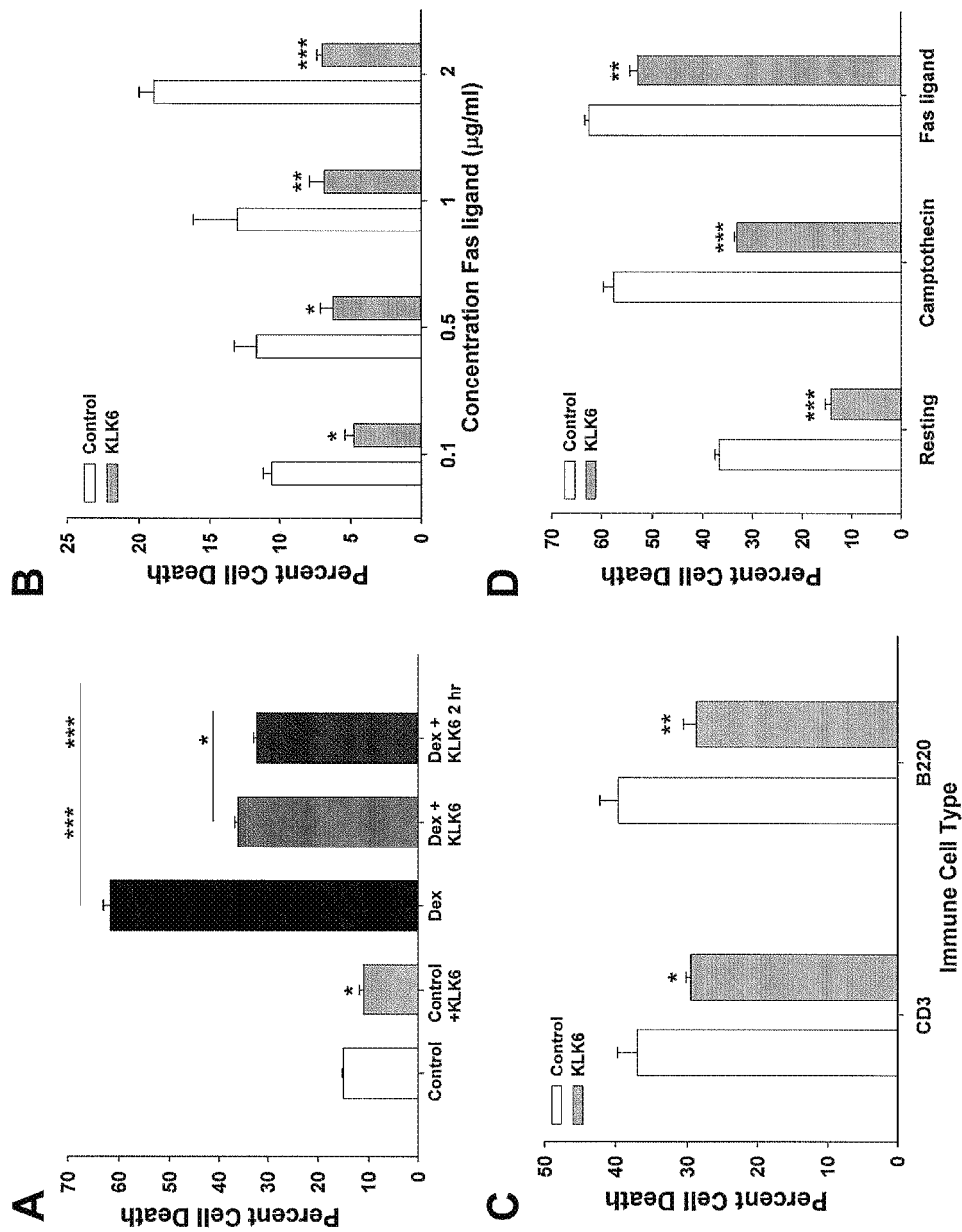
FIGS. 4A-D contain graphs demonstrating that KLK6 polypeptides block death of murine splenocytes and Jurkat T cells across multiple paradigms. KLK6 (10 µg/mL) significantly reduced the number of PI+ dead cells observed by flow cytometry after a 24-hour period in culture under resting conditions (A), in response to (0.1 µM) dexamethasone, or a 24-hour exposure to increasing concentrations of Fas ligand (FasL, B). In parallel experiments, Jurkat T cells exhibited significantly reduced levels of cell death under resting conditions and in response to camptothecin (1.0 µM) or Fas ligand (D, 2 µg/mL). KLK6 polypeptides blocked death of both CD3+ T cells and B220+ B cells under resting conditions (C). KLK6 polypeptides were applied at the time of plating in conjunction with cell death inducing agents in each case. A small but significant improvement in the ability of KLK6 polypeptides to rescue splenocytes from death was seen with a 2-hour pre-incubation prior to the addition of dexamethasone (A). Data are expressed as mean+SEM, One Way ANOVA with SNK post hoc test for multiple comparisons in FIG. 1A, two-way comparisons FIGS. 1A to D were made using Students t-test; $P<0.001*$, $P<0.005$, $P<0.02*$.
Figure 5:
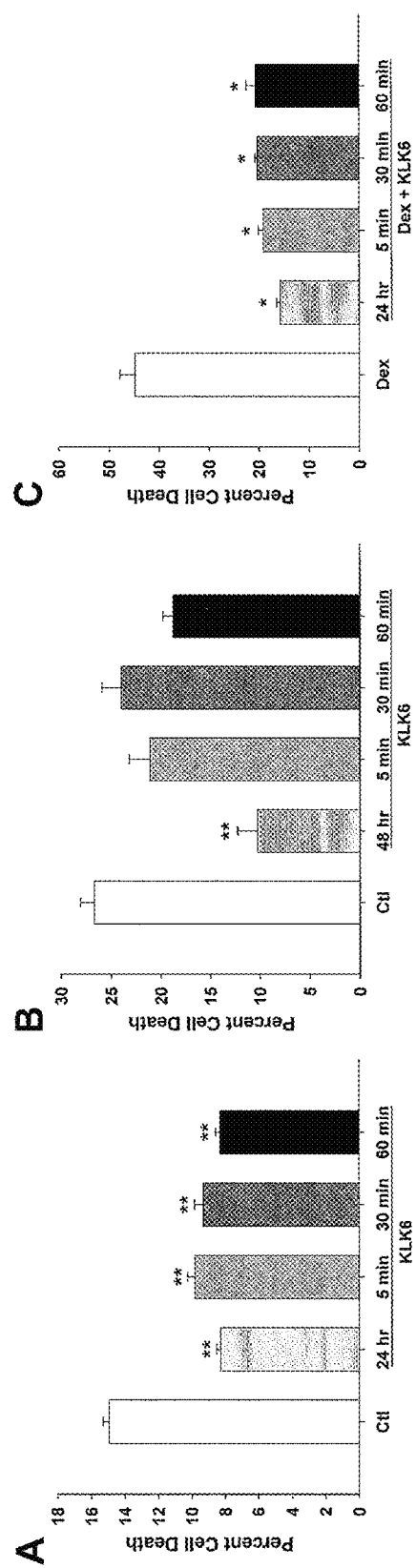
FIGS. 5A-C contain graphs demonstrating that as little as a 5-minute pulse of KLK6 polypeptides is sufficient to promote splenocyte survival. To gauge the minimal time of exposure to KLK6 polypeptides necessary to observe its pro-survival effects, splenocytes were pulsed with KLK6 (10 µg/mL) for periods of 5, 30, or 60 minutes, or in the presence of KLK6 polypeptides for the full 24- or 48-hour period of culture examined prior to labeling with PI for analysis of dead cells by flow cytometry (FIGS. 5A and B). A 5-minute pulse with KLK6 polypeptides promoted significant survival of explanted splenocytes over a 24-hour culture period that was similar in magnitude to that seen with longer pulses, i.e., 30 or 60 minutes and 24 hours (FIG. 5A). A 5-minute pulse with KLK6 polypeptides was also sufficient to promote survival when cells were exposed to dexamethasone (0.1 µM) for 24 hours (FIG. 5C). After longer periods of culture, however (FIG. 5B, 48 hours), only the more prolonged period of KLK6 polypeptide stimulation (48 hours) exerted significant pro-survival effects (FIG. 5B). Data are expressed as mean+SEM, One Way ANOVA with SNK post hoc test for multiple comparisons; $P<0.001**$, $P<0.005*$.
Figure 6:
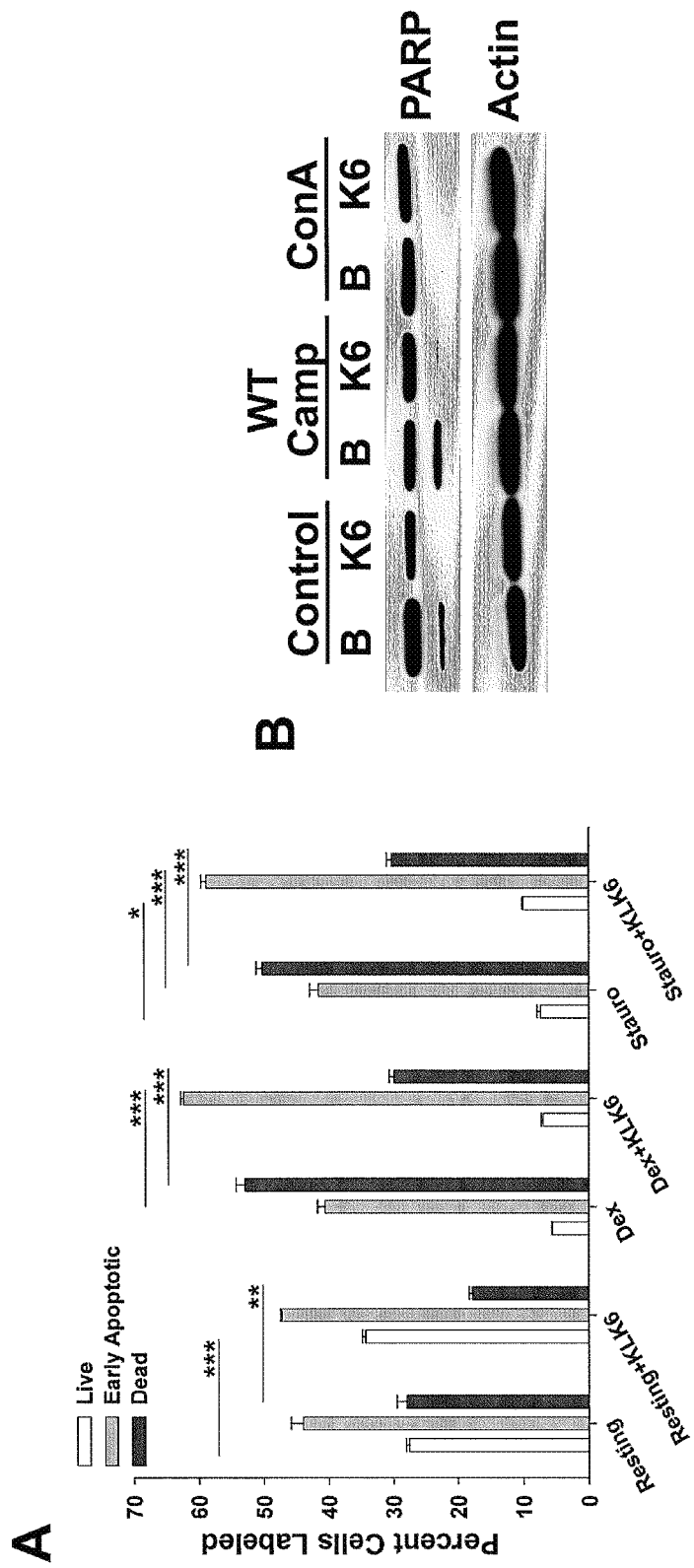
FIGS. 6A and B provide results demonstrating that the ability of KLK6 polypeptides to promote survival of murine splenocytes relates to its ability to block the apoptotic cascade.
FIG. 6B includes a photograph of a Western blot demonstrating that KLK6 polypeptides (10 µg/mL)-induced reductions in the amount of cleaved PARP observed in murine splenocytes cultured for a 24-hour period under resting conditions or in the presence of camptothecin (1.0 µM). The blot was re-probed for Actin to confirm loading accuracy.
Figure 7:
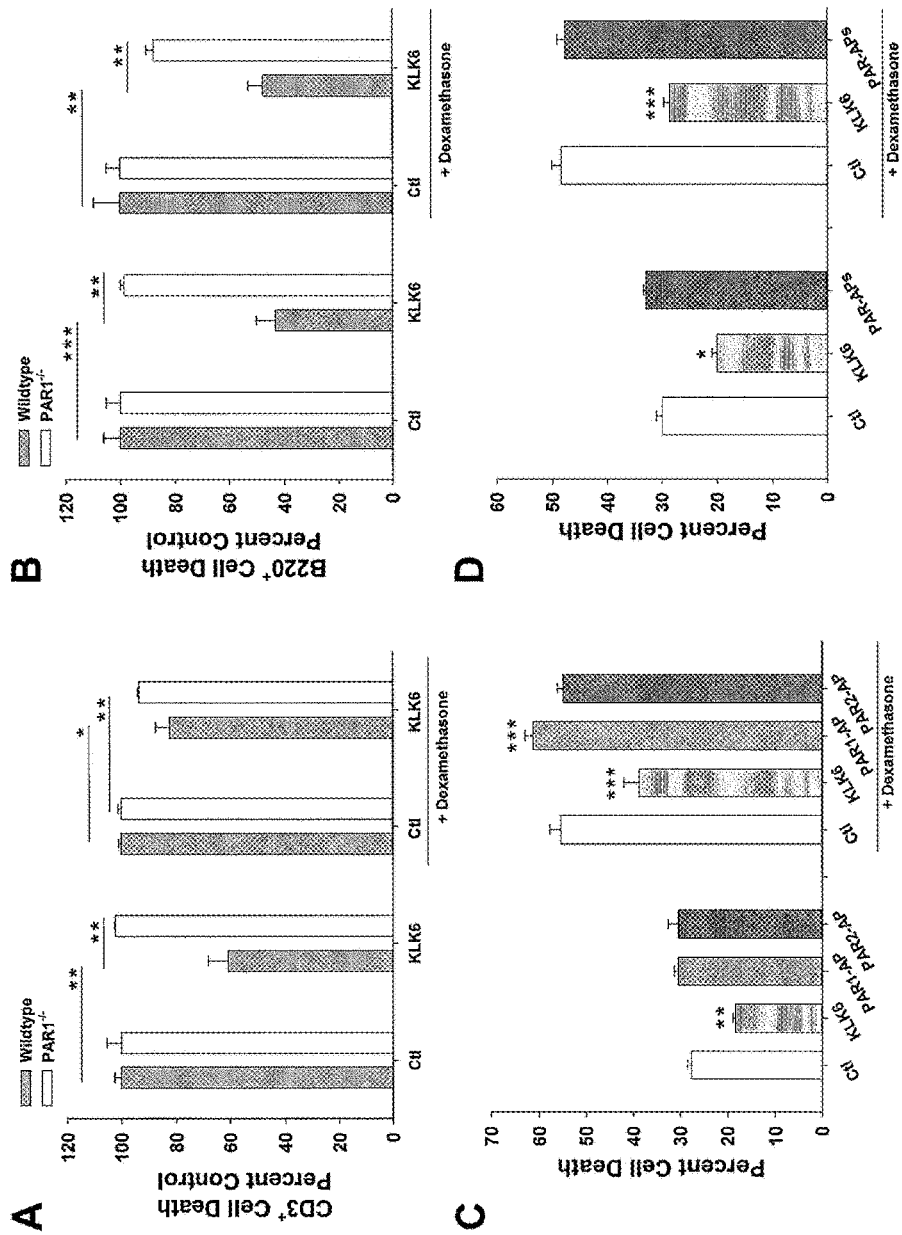
FIGS. 7A-D contain graphs demonstrating that the ability of KLK6 polypeptides to rescue murine T and B cells from death depends in part on activation of PAR1. To determine the involvement of PAR1 in KLK6-mediated lymphocyte rescue, the effects of KLK6 polypeptides (10 µg/mL) were compared between splenocytes harvested from wild type or PAR1–/– mice.
Figure 8:
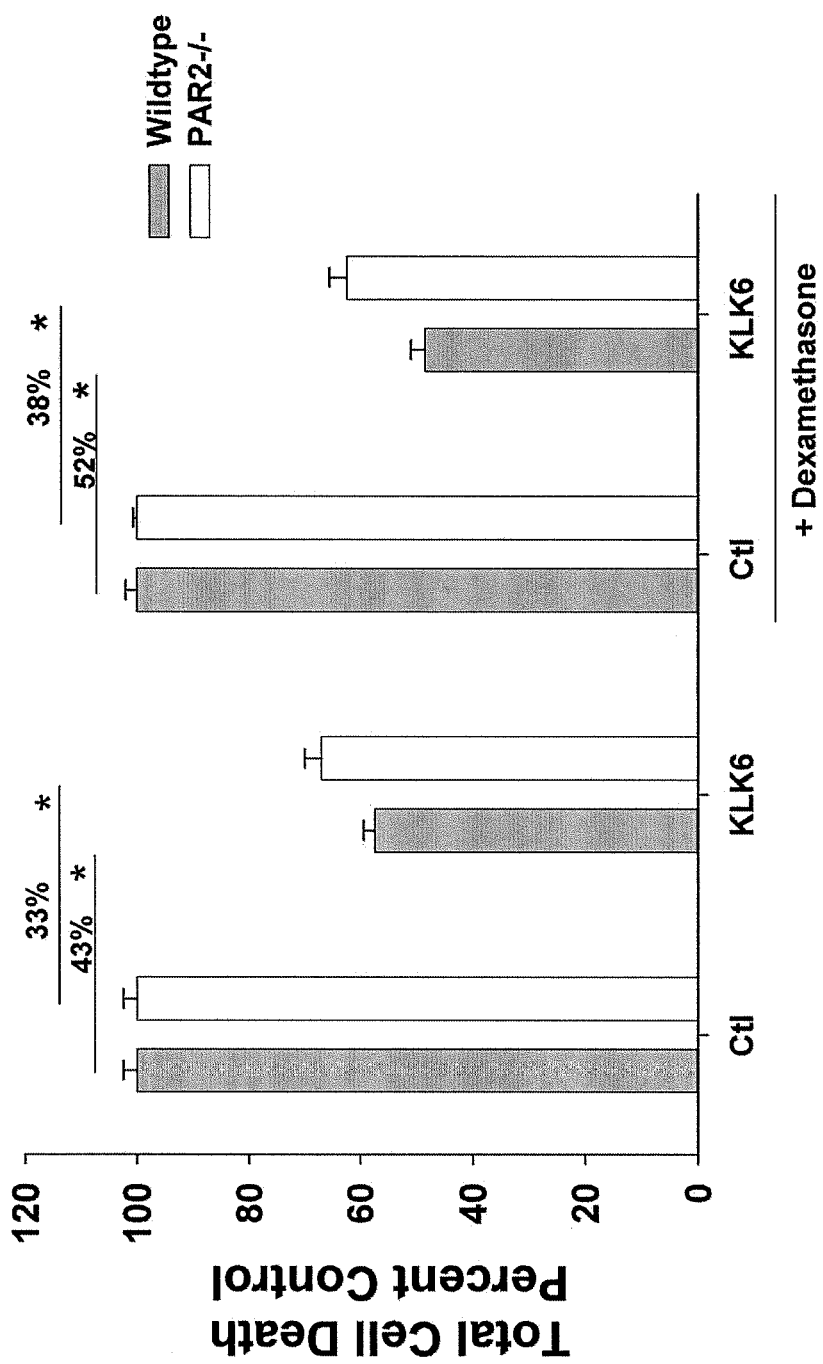
FIG. 8 is a bar graph plotting total cell death results that demonstrate that the ability of KLK6 to block lymphocyte cell death is reduced in the absence of the G-protein coupled receptor protease activated receptor 2 (PAR2). Recombinant KLK6 blocks death of murine lymphocytes under resting conditions and in the presence of 1 µg/mL dexamethasone. The extent of KLK6-mediated rescue is significantly reduced in lymphocytes derived from PAR2 deficient (−/−) mice (*$P<0.05$, Students t-test). Percent cell death was determined by quantification of propidium iodide labeled cells using flow cytometry. Results from 24 hour exposure times are shown.
Figure 9:
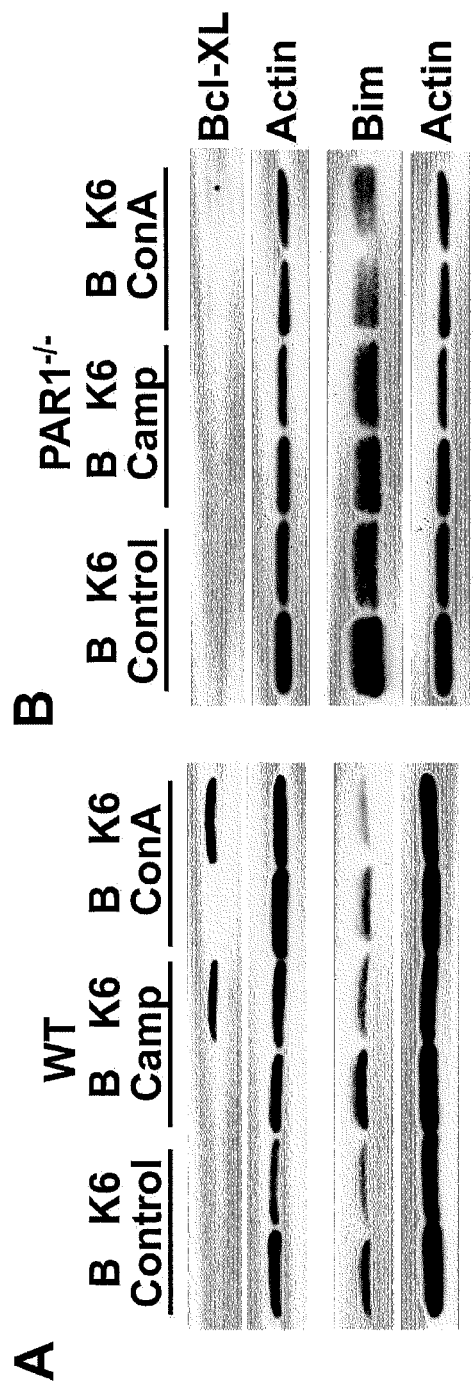
FIGS. 9A and B contain photographs of Western blot results demonstrating that KLK6 polypeptides differentially regulate Bcl2 family members in a PAR1 dependent fashion. In particular, the Western blots show the effect of KLK6 polypeptides on Bcl-XL and Bim in splenocytes derived from wild type and PAR1 deficient mice. KLK6 polypeptides promoted the expression of the pro-survival protein Bcl-XL in the presence of camptothecin or ConA (FIG. 9A), and this effect was abolished in the absence of PAR1 (FIG. 9B). KLK6 polypeptides also suppressed the expression of the pro-apoptotic protein Bim in all conditions examined (FIG. 9A), and this effect was reduced or absent in PAR1 deficient mice (FIG. 9B). Actin was used to control for loading in each case.
Figure 10:
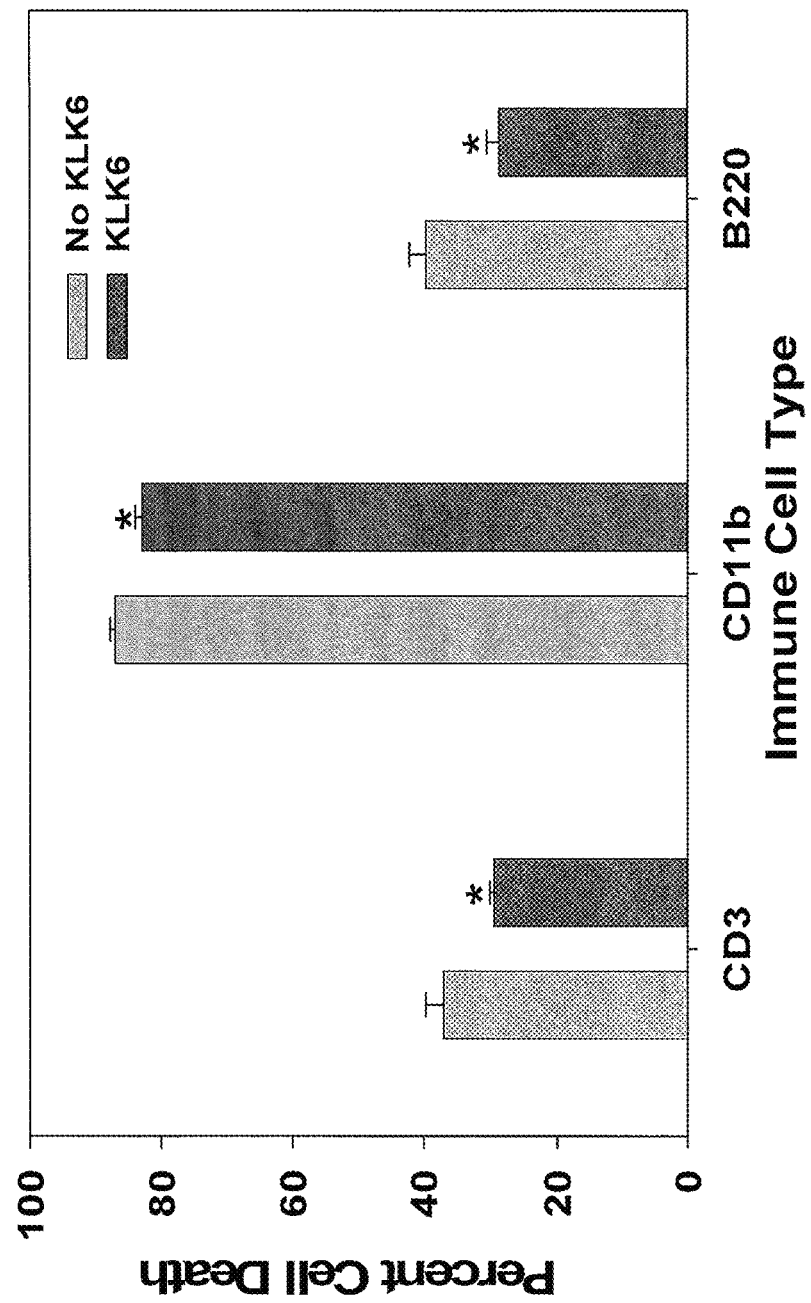
FIG. 10 is a graph plotting percent cell death of murine T cells (CD3+), monocytes (CD11b+), or B cells (B220+) treated with or without 10 µg/mL of recombinant KLK6 polypeptides. *=$P<0.05$ (One Way ANOVA, SNK post hoc test).
Figure 11:
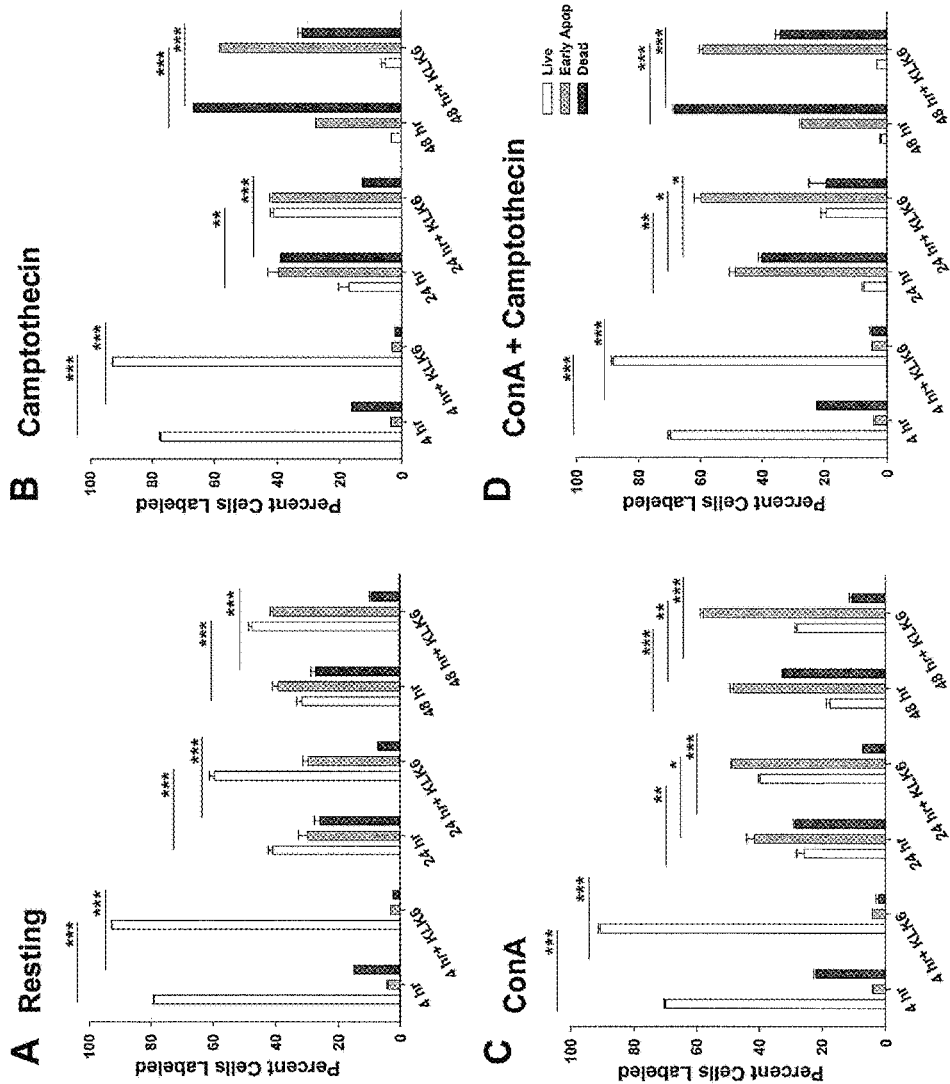
FIGS. 11A-D contain graphs demonstrating that KLK6 polypeptides promotes survival of Jurkat T cells in part by slowing the apoptotic cascade. To address the effect of KLK6 polypeptides on apoptosis, Jurkat cells were grown under resting conditions (FIG. 11A), or in the presence of apoptosis inducing agents (FIGS. 11B to D), then labeled with Annexin V-PE and 7-AAD prior to flow cytometry. Under resting conditions (FIG. 11A), and in the presence of camptothecin (FIG. 11B, 1.0 µM), ConA (FIG. 11C, 5 µg/mL), or ConA plus camptothecin (FIG. 11D), KLK6 polypeptides (10 µg/mL) promoted an increase in the number of live cells (unlabeled) and a decrease in the number of dead cells (Annexin V+ and 7AAD+) at both acute (4 hours), subacute (24 hours) and in some cases the more chronic time point examined (48 hours). In the presence of apoptosis inducing agents (FIGS. 11B to D), KLK6 polypeptides promoted a significant increase in the number of Jurkat cells positive for Annexin V, but negative for 7AAD, and therefore classified as in the early stages of apoptosis. Data are expressed as mean+SEM, One Way ANOVA with SNK post hoc test for multiple comparisons; $P<0.001$*, $P<0.005$, $P<0.02$*.
Figure 13:
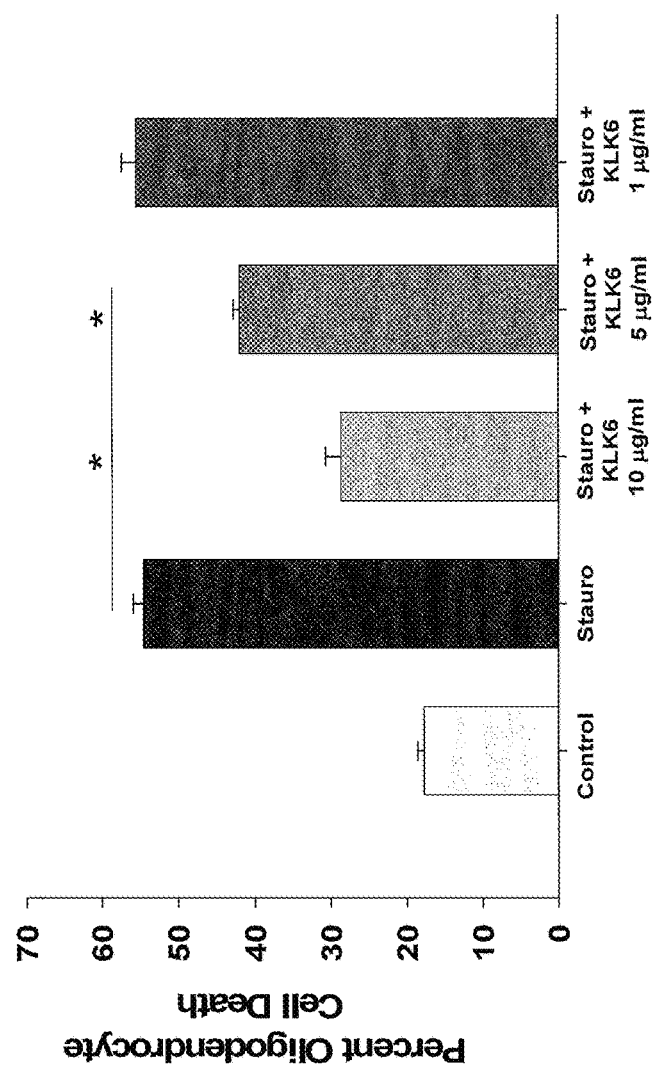
FIG. 13 is a graph plotting the percent of oligodendrocyte cell death for cells exposed to staurosporine (0.5 µM) in the absence or presence of recombinant KLK6 polypeptides (1, 5, or 10 µg/mL). *=$P<0.001$ (One Way ANOVA, SNK post hoc test).
Figure 14:
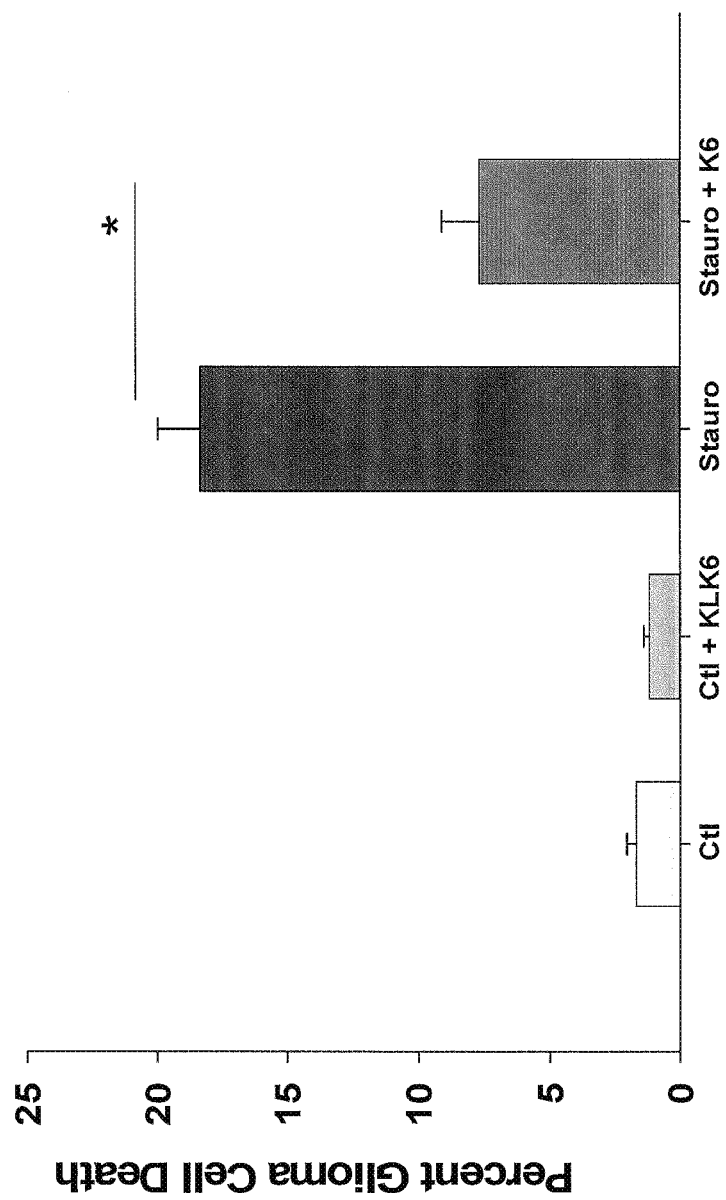
FIG. 14 is a graph plotting the percent of human glioma cell death for cells exposed to staurosporine (1 µM) in the absence or presence (pre-exposed to KLK6 polypeptides for 2 hour prior to application of staurosporine) of recombinant KLK6 polypeptides (10 µg/mL). *=$P<0.005$ (One Way ANOVA, SNK post hoc test).
Figure 15:
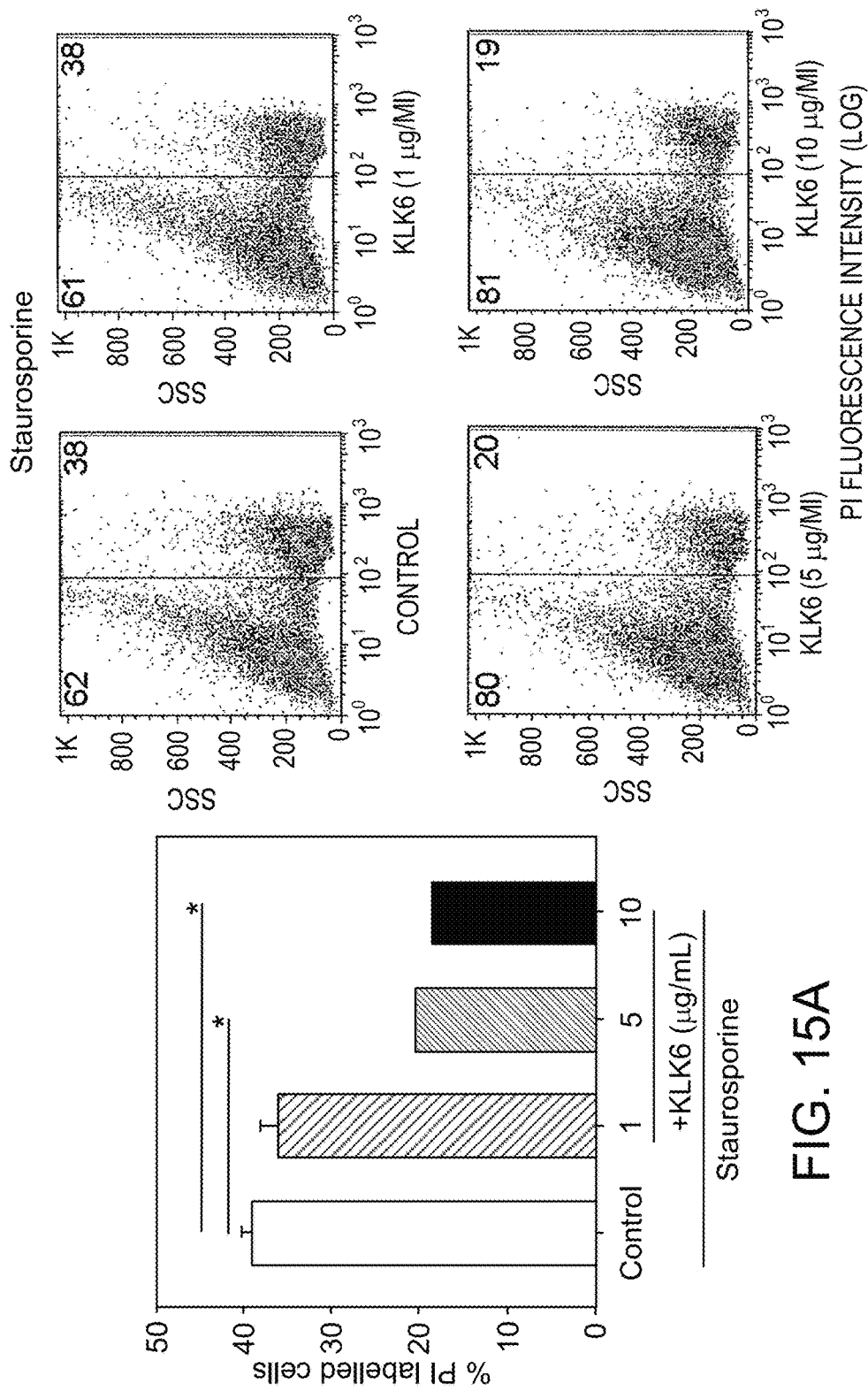
FIGS. 15A-B contain a graph (A) and flow cytometry results (B) demonstrating that recombinant KLK6 promotes the resistance of the U251 GBM cell line to the pan-protein kinase inhibitor Staurosporine in a dose dependent fashion (*$P<0.05$, Students t-test). The percent of cells labeled with propidium iodide (PI) after 24 hour exposure to staurosporine (1 µM) shown in histogram (FIG. 15A) was quantified by flow cytometry (FIG. 15B) and is taken as a measure of cell death. All samples were treated and analyzed in triplicate. Both 5 and 10 µg/mL recombinant KLK6 significantly reduced the amount of staurosporine induced cell death.
Figure 16:
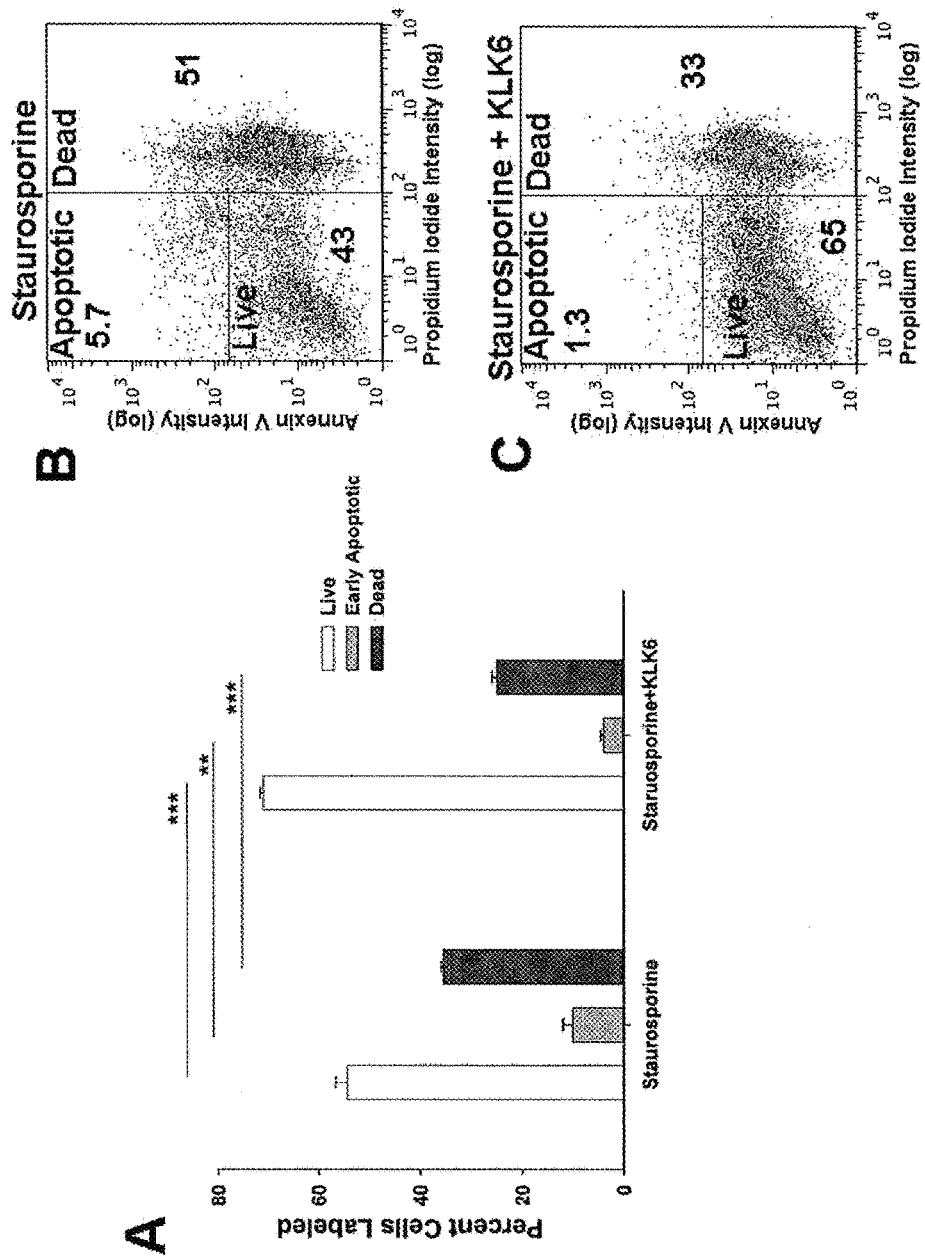
FIGS. 16A-C contain a graph (A) and flow cytometry results (B) and (C) demonstrating that recombinant KLK6 significantly reduces staurosporine-induced apoptosis of the U251 GBM line. Levels of live (Annexin V− and Propidium iodide− (PI−)), early apoptotic (Annexin V+ and PI−), or dead (Annexin V+ and PI+) cells were determined by flow cytometry after a 24 hour period of exposure to 1 µM staurosporine (FIG. 16B) or staurosporine in the presence of 10 µg/mL KLK6 (FIG. 16C). Histogram (FIG. 16A) shows quantification of three separate samples for each condition. KLK6 significantly increased the number of live cells and reduced the number of early apoptotic and dead cells (*P<0.05, Students t-test).
Figure 17:
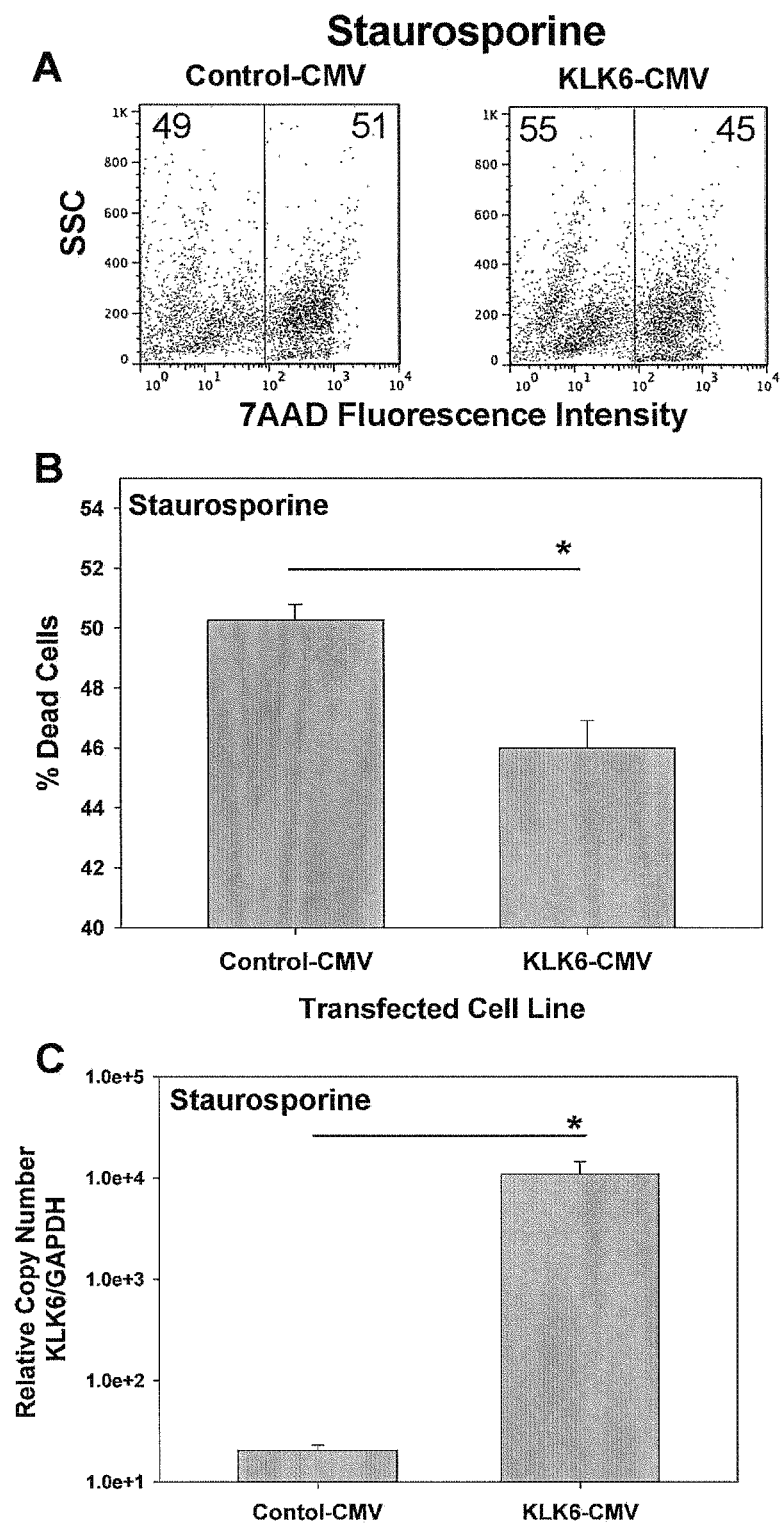
FIGS. 17A-C contain results demonstrating that KLK6 over expression promotes resistance of the U251 GBM cell line to staurosporine induced death.
Figure 18:
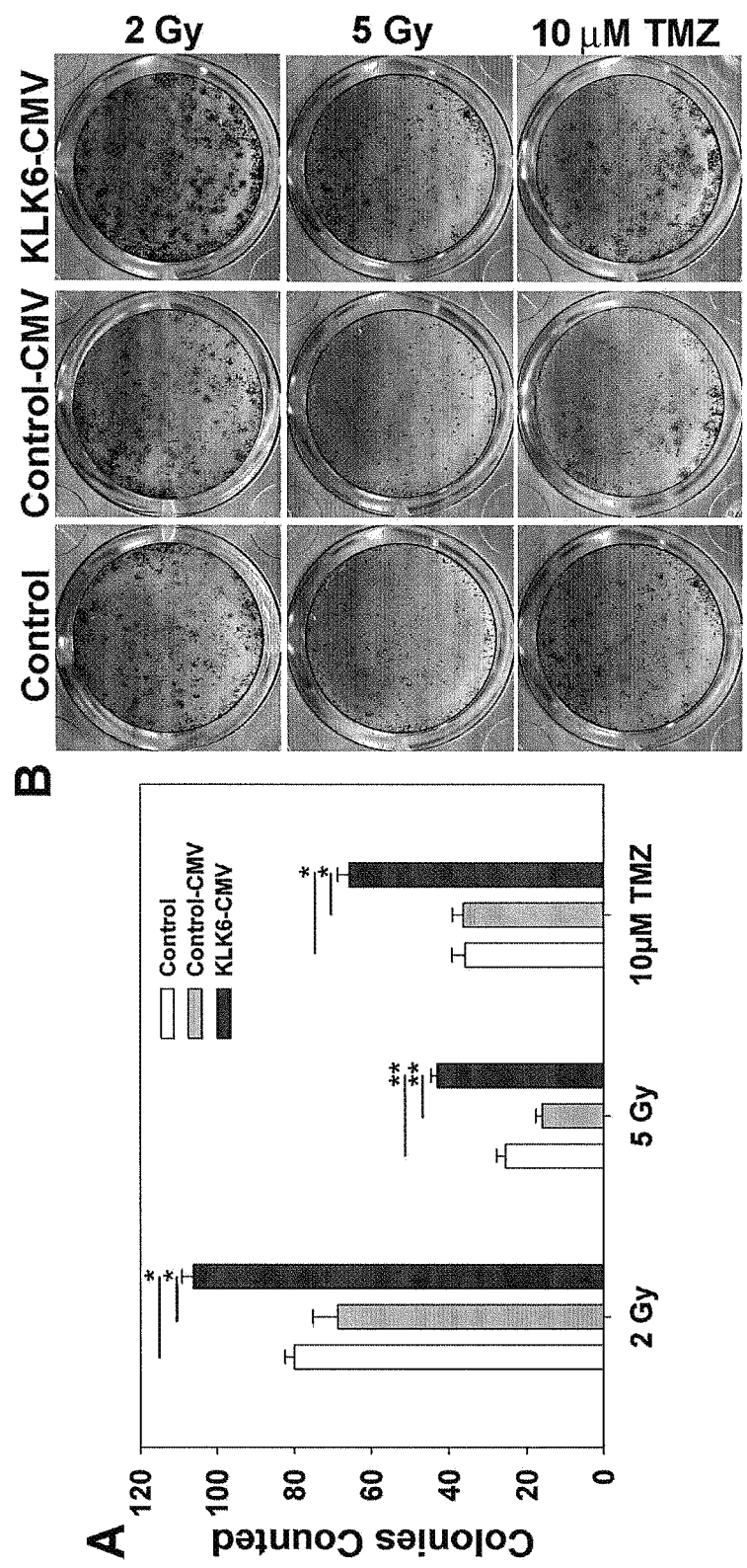
FIGS. 18A-B contain results demonstrating that U251 GBM cells over expressing KLK6 were associated with increased resistance to treatment with radiation (RT) or temozolomide (TMZ). Control U251 GBM cells or U251 cells transfected with an empty control-CMV vector, or with a KLK6-CMV vector were plated at low density, treated with 2 or 5 Gy of ionizing radiation, or with 10 µM TMZ for 24 hours and then allowed to proliferate for 2 weeks in culture. Cellular colonies formed were then fixed with acidic crystal violet (FIG. 18B), and the number of colonies formed was quantified as shown in histogram (FIG. 18A). U251 cells over expressing KLK6 (KLK6-CMV) were significantly more resistant to either 2 or 5 Gy radiation, or TMZ, as reflected in an increased number of colonies counted (*P<0.05, Students t-test).
Figure 19:
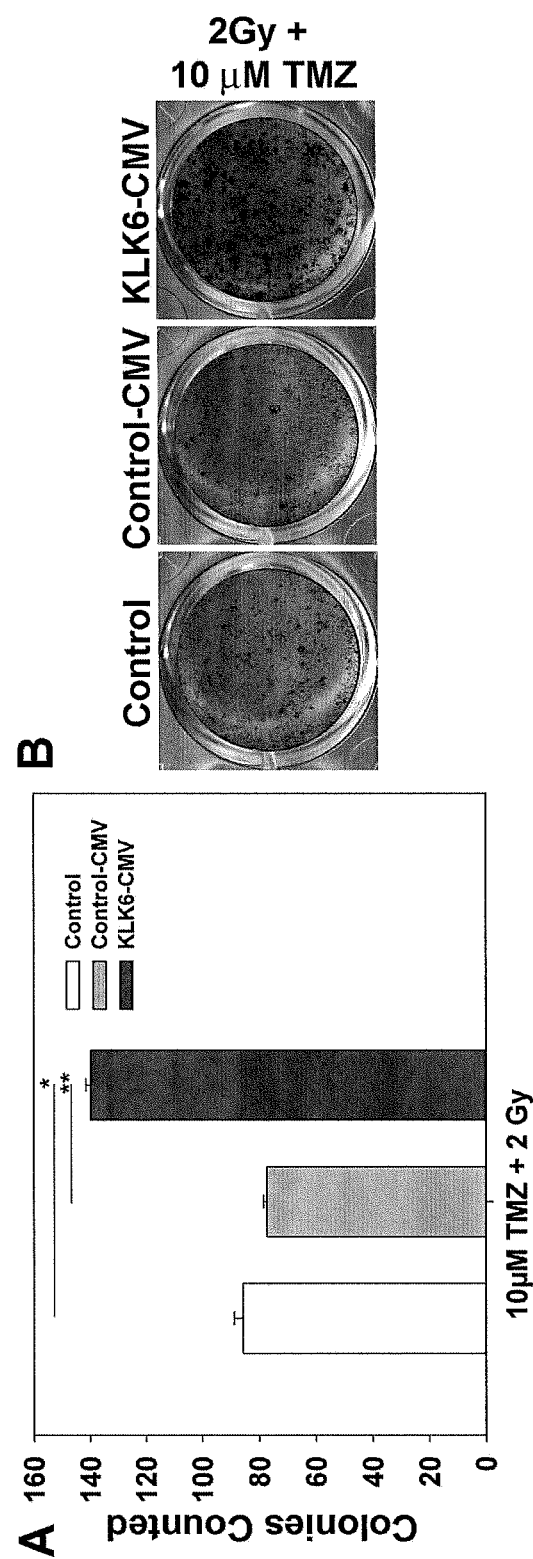
FIGS. 19A-B contain results demonstrating that U251 GBM cells over expressing KLK6 were resistant to combined treatment with radiation (RT) and temozolomide (TMZ), the current standard of care for patients with GBM. Control U251 GBM cells, or U251 cells transfected with an empty control-CMV vector, or with a KLK6-CMV vector were plated at low density, treated with 2 Gy of ionizing radiation and 10 µM TMZ (24 hours), and then allowed to proliferate for 2 weeks in culture. Colonies formed were then fixed with acidic crystal violet (FIG. 19B), and the number of colonies formed was quantified as shown in histogram (FIG. 19A). U251 cells over expressing KLK6 (KLK6-CMV) were significantly more resistant to combined treatment with RT and TMZ as reflected in an increased number of colonies counted (*P<0.05, Students t-test).
Figure 20:
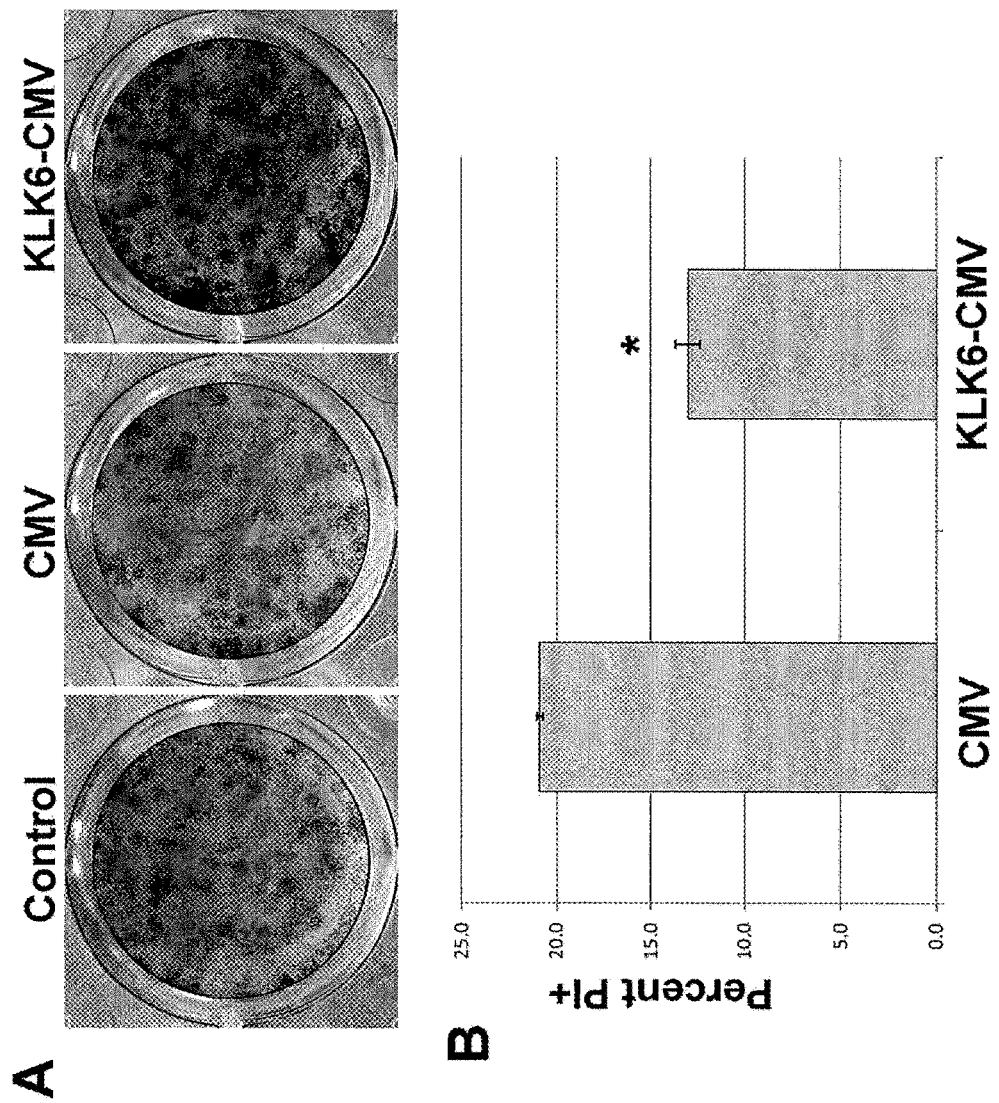
FIGS. 20A-B contain results demonstrating that U251 GBM cells over expressing KLK6 were associated with increased resistance to treatment with the chemotherapeutic agent, Cisplatin. Control U251 GBM cells or U251 cells transfected with an empty control-CMV vector, or with a KLK6-CMV vector were plated at low density, treated with 10 µg/mL of Cisplatin for 24 hours, and then allowed to proliferate for 2 weeks in culture. Colonies formed were then fixed with acidic crystal violet (FIG. 20A), and the number of colonies formed quantified. Significantly more colonies were seen in GBM cells over expressing KLK6.

This document provides methods and materials involved in modulating a cell's ability to be resistant to apoptosis. As described herein, KLK6 polypeptide activity can either be increased to reduce apoptosis, or inhibited to promote apoptosis. For example, this document provides methods and materials for exposing cells to kallikrein 6 (KLK6) polypeptides, or increased KLK6 polypeptide activity, to promote resistance to apoptosis. As described herein, the exposure of cells to KLK6 polypeptides promotes the survival of those cells under resting conditions and/or under conditions that normally promote apoptosis. Examples of cells that can be exposed to a KLK6 polypeptide (or increased KLK6 polypeptide activity) include, without limitation, lymphocytes (e.g., T cells or B cells), monocytes, oligodendrocytes, astrocytes, glioma cells, epidermal cells, or stem cells. Any appropriate mammal can be treated using the methods and materials described herein. For example, mammals such as humans, monkeys, dogs, cats, cows, horses, pigs, rats, and mice can be treated as described herein.

As described herein, KLK6 polypeptides, molecules designed to increase KLK6 polypeptide expression levels, and molecules designed to increase KLK6 polypeptide activity can be used to treat conditions that exhibit undesirable apoptosis. For example, conditions and diseases that involve too much cell death can be treated using KLK6 polypeptides, molecules designed to increase KLK6 polypeptide expression, or molecules designed to increase KLK6 polypeptide activity. Examples of such conditions and diseases include, without limitation, immunodeficiency disorders (e.g., immunodeficiency disorders induced by HIV infections), anemia, lymphyopenia, and sepsis. In some cases, an abnormal loss of neurons and glia associated with a neurodegenerative disease such as Huntington's disease, Parkinson's disease, Alzheimer's disease, and retinal/macular degeneration can be reduced by administering KLK6 polypeptides, molecules designed to increase KLK6 polypeptide expression, and/or molecules designed to increase KLK6 polypeptide activity. In some cases, excessive apoptosis can occur during heart failure, stroke, liver injury, kidney disease, multiple organ dysfunction syndrome, and bone disorders. In such cases, KLK6 polypeptides, molecules designed to increase KLK6 polypeptide expression, and/or molecules designed to increase KLK6 polypeptide activity can be administered to reduce cell death, thereby reducing the severity of one or more symptoms of these conditions.

In some cases, KLK6 polypeptides, molecules designed to increase KLK6 polypeptide expression, and/or molecules designed to increase KLK6 polypeptide activity can be used to promote resistance to cell death that occurs with ischemic injury to tissues including, without limitation, muscle, heart, brain, and gastrointestinal tissue. In some cases, KLK6 polypeptides, molecules designed to increase KLK6 polypeptide expression, and/or molecules designed to increase KLK6 polypeptide activity can be used to reduce apoptosis and promote cell survival to enhance tissue regeneration, to improve responses to immunological adjuvants, and to enhance stem cell therapy.

In some cases, KLK6 polypeptides, molecules designed to increase KLK6 polypeptide expression, and/or molecules designed to increase KLK6 polypeptide activity can be used to reduce excessive apoptosis that can occur in trophoblast cells of the placenta as they invade the uterine environment, thereby preventing complications of pregnancy such as preeclampsia. In some cases, KLK6 polypeptides, molecules designed to increase KLK6 polypeptide expression, and/or molecules designed to increase KLK6 polypeptide activity can be used to promote cardiac, skeletal, or vascular muscle cell survival. For example, KLK6 polypeptides can be used to promote bone cell survival, thereby preventing osteoporosis and/or promoting bone and cartilage repair and regeneration. In some cases, KLK6 polypeptides, molecules designed to increase KLK6 polypeptide expression, and/or molecules designed to increase KLK6 polypeptide activity can be used to reduce cell death that occurs with aging.

In some cases, conditions or exposures known to induce apoptosis (e.g., withdrawal of growth factors, activation of cell surface death receptors, exposure to heat shock, hypoxia, UV radiation, DNA damage, viral infection, dexamethasone, cytotoxic agents, or chemotherapeutic agents) can be treated by administering KLK6 polypeptides, molecules designed to increase KLK6 polypeptide expression, and/or molecules designed to increase KLK6 polypeptide activity. For example, a composition containing KLK6 polypeptides can be used to treat severe sunburns, thereby reducing the level of apoptosis that occurs. In some cases, cancer therapeutics such as chemotherapeutic agents known to induce apoptosis of cells (e.g., mucosal membrane cells, lymphocytes, leukocytes, and hair follicles) can be administered with KLK6 polypeptides, molecules designed to increase KLK6 polypeptide expression levels, and/or molecules designed to increase KLK6 polypeptide activity to reduce the level of general apoptosis induced by the cancer therapeutic. Examples of such cancer therapeutics include, without limitation, alkylating agents such as Cisplatin, vinca alkaloids such as Vincristine, Taxanes such as Taxonl, topoisomerase inhibitors such as camptothecin and topotecan, anti-neoplastics such as doxorubicin, and anti-metabolites. In such cases, the composition including a KLK6 polypeptide, molecule designed to increase KLK6 polypeptide expression, and/or molecule designed to increase KLK6 polypeptide activity can be administered prior to, with, or after administration of the cancer therapeutic.

In some cases, KLK6 polypeptides, molecules designed to increase KLK6 polypeptide expression, and/or molecules designed to increase KLK6 polypeptide activity can be used to inhibit the pro-apoptotic protein Bim and to enhance levels of the anti-apoptotic protein Bcl-XL.

In some cases, cells within a mammal can be exposed a composition containing KLK6 polypeptides to promote resistance to apoptosis. In some cases, the level of KLK6 polypeptide expression or activity can be increased by administering a KLK6 polypeptide agonist or a nucleic acid encoding a KLK6 polypeptide. Such a nucleic acid can encode a full-length KLK6 polypeptide such as a human KLK6 polypeptide having the amino acid sequence set forth in FIG. 22B, or a biologically active fragment of a KLK6 polypeptide having amino acid residues 22 to 244 of the sequence set forth in FIG. 22B. See, also, GenBank® Accession No. NM_002774 (GI No. 61744422); Bernett et al., *J. Biol. Chem.*, 277:24562-24570 (2002) and Blaber et al., *Biochemistry*, 41:1165-1173 (2002)). A nucleic acid encoding a KLK6 polypeptide or fragment thereof can be administered to a mammal using any appropriate method. For example, a nucleic acid can be administered to a mammal using a vector such as a viral vector.

Vectors for administering nucleic acids (e.g., a nucleic acid encoding a KLK6 polypeptide or fragment thereof) to a mammal are known in the art and can be prepared using standard materials (e.g., packaging cell lines, helper viruses, and vector constructs). See, for example, *Gene Therapy Protocols (Methods in Molecular Medicine)*, edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses. Lentiviruses are a genus of retroviruses that can be used to infect cells (e.g., cancer cells). Adenoviruses contain a linear double-stranded DNA genome that can be engineered to inactivate the ability of the virus to replicate in the normal lytic life cycle. Adenoviruses and adeno-associated viruses can be used to infect cancer cells.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a KLK6 polypeptide or fragment thereof. A viral vector can be replication-competent or replication-defective, and can contain fewer viral genes than a corresponding wild-type virus or no viral genes at all.

In addition to nucleic acid encoding a KLK6 polypeptide or fragment thereof, a viral vector can contain regulatory elements operably linked to a nucleic acid encoding a KLK6 polypeptide or fragment thereof. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a KLK6 polypeptide or fragment thereof. A promoter can be constitutive or inducible (e.g., in the presence of tetracycline), and can affect the expression of a nucleic acid encoding a KLK6 polypeptide or fragment thereof in a general or tissue-specific manner. Tissue-specific promoters include, without limitation, enolase promoter, prion protein (PrP) promoter, and tyrosine hydroxylase promoter.

As used herein, "operably linked" refers to positioning of a regulatory element in a vector relative to a nucleic acid in such a way as to permit or facilitate expression of the encoded polypeptide. For example, a viral vector can contain a neuronal-specific enolase promoter and a nucleic acid encoding a KLK6 polypeptide or fragment thereof. In this case, the enolase promoter is operably linked to a nucleic acid encoding a KLK6 polypeptide or fragment thereof such that it drives transcription in neuronal cells.

A nucleic acid encoding a KLK6 polypeptide or fragment thereof also can be administered to cells using non-viral vectors. Methods of using non-viral vectors for nucleic acid delivery are known to those of ordinary skill in the art. See, for example, *Gene Therapy Protocols* (*Methods in Molecular Medicine*), edited by Jeffrey R. Morgan, Humana Press, Totowa, N.J. (2002). For example, a nucleic acid encoding a KLK6 polypeptide or fragment thereof can be administered to a mammal by direct injection of nucleic acid molecules (e.g., plasmids) comprising nucleic acid encoding a KLK6 polypeptide or fragment thereof, or by administering nucleic acid molecules complexed with lipids, polymers, or nanospheres.

A nucleic acid encoding a KLK6 polypeptide or fragment thereof can be produced by standard techniques, including, without limitation, common molecular cloning, polymerase chain reaction (PCR), chemical nucleic acid synthesis techniques, and combinations of such techniques. For example PCR or RT-PCR can be used with oligonucleotide primers designed to amplify nucleic acid (e.g., genomic DNA or RNA) encoding a KLK6 polypeptide or fragment thereof. In some cases, the methods described elsewhere can be used to make or use nucleic acid encoding a KLK6 polypeptide or biologically active fragment thereof (see, e.g., Bernett et al., *J. Biol. Chem.*, 277:24562-24570 (2002) and Blaber et al., *Biochemistry*, 41:1165-1173 (2002)).

This document also provides methods and materials for reducing the ability of KLK6 polypeptides to promote resistance to apoptosis. For example, an inhibitor of KLK6 polypeptide activity can be used to reduce KLK6 polypeptide-induced resistance to apoptosis. As described herein, KLK6 polypeptide inhibitors and molecules designed to reduce KLK6 polypeptide expression can be used to treat conditions and diseases that exhibit undesirable resistance to apoptosis. Examples of KLK6 polypeptide inhibitors include, without limitation, KLK6 antisense molecules, KLK6 small hairpin RNA target molecules, KLK6-specific miRNA molecules, function blocking anti-KLK6 antibodies (e.g., mK6-2 and mK6-3 antibodies (Blaber et al., *FASEB J.*, 19:920-922 (2004)), pharmacologic KLK6-specific inhibitors, and combinations thereof. Examples of KLK6 small hairpin RNA target molecules include, without limitation, GAGCAGAATAAG-TTGGTGCAT (SEQ ID NO:3), CCTCTACACCTCGGGCCACTT (SEQ ID NO:4), AGC-CAAACTCTCTGAACTCAT (SEQ ID NO:5), and GAT-GAGAAGTACG-GGAAGGAT (SEQ ID NO:6). See, also, Henkhaus et al., *Biological Chemistry*, 389: 757-764 (2008)). Examples of KLK6-specific miRNA molecules include, without limitation, hsa-let-7f-1 and hsa-let-7f-2 (Chow et al., *Biological Chemistry*, 389:731-738 (2008)). In some cases, blockade of the receptor complement that KLK6 activates, which is known to include protease activated receptors 1 (PAR1) and PAR2 and bradykinin receptor 2 (B2) can be used to reduce apoptosis resistance.

Antibodies having specific binding affinity for a KLK6 polypeptide can be used to inhibit KLK6 polypeptide activity (e.g., decrease activity). As used herein, the terms "antibody" or "antibodies" include intact molecules as well as fragments thereof that are capable of binding to an epitopic determinant of a KLK6 polypeptide (e.g., human KLK6 polypeptide). The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for a KLK6 polypeptide can be generated by known techniques. For example, F(ab')$_2$ fragments can be produced by pepsin digestion of the antibody molecule; Fab fragments can be generated by reducing the disulfide bridges of F(ab')$_2$ fragments. Alternatively, Fab expression libraries can be constructed. See, for example, Huse et al., *Science*, 246:1275 (1989). Once produced, antibodies or fragments thereof are tested for recognition of a KLK6 polypeptide by standard immunoassay methods including ELISA techniques, radioimmunoassays, and Western blotting. See, Short Protocols in Molecular Biology, Chapter 11, Green Publishing Associates and John Wiley & Sons, Edited by Ausubel, F. M et al., 1992.

Antibodies having specific binding affinity for a KLK6 polypeptide can be produced through standard methods. In general, a KLK6 polypeptide can be recombinantly produced, or can be purified from a biological sample, and used to immunize animals. To produce a recombinant KLK6 polypeptide, a nucleic acid sequence encoding a KLK6 polypeptide can be ligated into an expression vector and used to transform a bacterial or eukaryotic host cell. Nucleic acid constructs typically include a regulatory sequence operably linked to a KLK6 nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express a KLK6 polypeptide can be produced by using expression vectors with the appropriate control elements and a selectable marker. For example, the eukaryotic expression vector pCDNA.3.1+ (Invitrogen, San Diego, Calif.) is suitable for expression of a KLK6 polypeptide in, for example, COS cells, Chinese hamster ovary (CHO), or HEK293 cells. Following introduction of the expression vector by electroporation, DEAE dextran, or other suitable method, stable cell lines are selected. Alternatively, a KLK6 polypeptide can be transcribed and translated in vitro using wheat germ extract or rabbit reticulocyte lysase.

In eukaryotic host cells, a number of viral-based expression systems can be utilized to express a KLK6 polypeptide.

A nucleic acid encoding a KLK6 polypeptide can be introduced into a SV40, retroviral or vaccinia based viral vector and used to infect host cells.

Various host animals can be immunized by injection of a KLK6 polypeptide. Host animals include, without limitation, rabbits, chickens, mice, guinea pigs, and rats. Various adjuvants that can be used to increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin and dinitrophenol. Monoclonal antibodies can be prepared using a KLK6 polypeptide and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy", Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

In some embodiments, anti-KLK6 antibodies can inhibit the enzymatic activity of a KLK6 polypeptide. In vitro assays can be used to monitor KLK6 polypeptide activity after incubation in the presence of an antibody. Typically, a KLK6 polypeptide can be incubated with an antibody (e.g., polyclonal or monoclonal), then the ability of the KLK6 polypeptide to cleave a substrate such as myelin basic protein or an arginine-specific fluorogenic substrate can be assessed at 37° C. in a suitable buffer (e.g., Tris buffer). Depending on the substrate, cleavage can be monitored using sodium dodecyl sulfate (SDS)-polyacrylamide gel electrophoresis (PAGE) or a spectrophotometer.

Antisense oligonucleotides can be used to reduce expression of a KLK6 polypeptide. A KLK6 antisense oligonucleotide can be at least 8 nucleotides in length. For example, a KLK6 antisense oligonucleotide can be about 8, 9, 10-20 (e.g., 11, 12, 13, 14, 15, 16, 17, 18, 19, or 20 nucleotides in length), 15 to 20, 18-25, or 20-50 nucleotides in length. In other embodiments, KLK6 antisense oligonucleotides can be used that are greater than 50 nucleotides in length, including the full-length sequence of a KLK6 mRNA. As used herein, the term "oligonucleotide" refers to an oligomer or polymer of ribonucleic acid (RNA) or deoxyribonucleic acid (DNA) or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller, *Antisense Nucleic Acid Drug Dev.*, 7:187-195 (1997); and Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863, 5,235,033, 5,750,666, and 5,596,086 for methods of preparing oligonucleotides with modified backbones.

In some cases, KLK6 antisense oligonucleotides can be modified by chemical linkage to one or more moieties or conjugates that enhance the activity, cellular distribution or cellular uptake of the oligonucleotide. Such moieties include but are not limited to lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

Methods for synthesizing antisense oligonucleotides are known, including solid phase synthesis techniques. Equipment for such synthesis is commercially available from several vendors including, for example, Life Technologies (AKA, Applied Biosystems; Foster City, Calif.). Alternatively, expression vectors that contain a regulatory element that directs production of an antisense transcript can be used to produce antisense molecules.

KLK6 antisense oligonucleotides can bind to a nucleic acid encoding a KLK6 polypeptide, including DNA encoding KLK6 RNA (including pre-mRNA and mRNA) transcribed from such DNA, and also cDNA derived from such RNA, under physiological conditions (i.e., physiological pH and ionic strength). The nucleic acid sequence encoding a human KLK6 polypeptide can be found in GenBank® under Accession No. AF013988 (GI No. 2318114), AF149289 (GI No. 5791635), D78203 (GI No. 1805492), or NM_002774 (GI No. 61744422). The nucleic acid sequence encoding a rat KLK6 polypeptide can be found in GenBank® under Accession No. AF016269 (GI No. 2853365). The nucleic acid sequence encoding a mouse KLK6 polypeptide can be found in GenBank® under Accession No. NM_019175.1 (GI No. 9506996). For example, an antisense oligonucleotide can hybridize under physiological conditions to the nucleotide sequence set forth in GenBank Accession No. AF013988, AF149289, 78203, NM_002774, AF016269, or NM_019175.1.

is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the KLK6 nucleic acid interferes with the normal function of the KLK6 nucleic acid, and non-specific binding to non-target sequences is minimal.

Target sites for KLK6 antisense oligonucleotides include the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a KLK6 nucleic acid can be evaluated by measuring levels of the KLK6 mRNA or polypeptide (e.g., by Northern blotting, RT-PCR, Western blotting, ELISA, or immunohistochemical staining).

Examples of conditions that can be treated by promoting apoptosis via inhibition of KLK6 polypeptide expression or activity include, without limitation, inflammatory conditions (e.g., rheumatoid arthritis, Crohn's disease, multiple sclerosis, systemic lupus erythematosus, and psoriasis), lymphoproliferative diseases (e.g., follicular lymphoma, chronic lymphocytic leukemia, acute lymphoblastic leukemia, hair cell leukemia, lymphomas, multiple myeloma, Waldenstrom's macroglobulinemia, Wiskott-Aldrich syndrome, post-transplant lymphoproliferative disorder, Autoimmune lymphoproliferative syndrome, and lymphoid interstitial pneumonia), cancer (e.g., solid tumor cancers and blood cancers), infectious diseases (e.g., viral, bacterial, fungal, parasitic, protozoal, and prion infections), and cardiovascular diseases (e.g., coronary heart disease, cardiomyopathy, ischemic heart disease, heart failure, hypertensive heart disease, inflammatory heart disease, and valvular heart disease). Since KLK6 polypeptides exhibit pro-survival effects on human glioma cells, inhibition of KLK6 polypeptide can be used to reduce tumor cell survival, thereby promoting tumor regression and making tumor cells more susceptible to current therapies, including radiation and chemotherapy. In some cases, KLK6 polypeptide inhibitors can be used to increase apoptosis in solid tumors such as gliomas, lung cancer, bladder cancer, breast cancer, colon cancer, head and neck cancer, pancreatic cancer, cervical cancer, prostate cancer, and skin cancer, or blood cancers such as leukemias and lymphomas. In some cases, reducing KLK6 polypeptide levels or activity can be used to improve apoptosis for application in tissue remodeling and/or tissue regeneration such as organ/bone repair, scar reduction, or fat cell removal. In some cases, a lymphoproliferative disease, cancer, infection, or cardiovascular disease treated as described herein with a KLK6 polypeptide inhibitor can be a non-inflammatory condition.

Any appropriate method can be used to administer a KLK6 polypeptide inhibitor to reduce resistance to apoptosis. For example, an effective amount of a composition containing KLK6 polypeptide inhibitor can be administered to a mammal by any route, including, without limitation, oral or parenteral routes of administration such as intravenous, intramuscular, intraperitoneal, subcutaneous, intrathecal, intraarterial, nasal, transdermal (e.g., as a patch), or pulmonary absorption. An effective amount of a KLK6 polypeptide inhibitor can be an amount that reduces resistance to apoptosis without inducing significant toxicity to the host. Effective amounts of KLK6 polypeptide inhibitors can be determined by a physician, taking into account various factors that can modify the action of drugs such as overall health status, body weight, sex, diet, time and route of administration, other medications, and any other relevant clinical factors.

A KLK6 polypeptide inhibitor can be formulated as, for example, a solution, suspension, or emulsion with pharmaceutically acceptable carriers or excipients suitable for the particular route of administration, including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives, flavorings, sugars, and other additives such as antimicrobials, antioxidants, chelating agents, inert gases, and the like also may be present.

For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

In some embodiments, anti-cancer agents can be administered in combination with a KLK6 polypeptide inhibitor. For example, an anti-cancer agent such as temazolamide, avastin, taxol, or radiation can be administered to a mammal together with a KLK6 polypeptide inhibitor.

This document also provides methods and materials related to identifying agonists or antagonists of KLK6 polypeptide activity (e.g., pro-survival activity). For example, candidate molecules can be screened to identify KLK6 polypeptide inhibitors that can block the ability of KLK6 polypeptides to rescue cells from apoptosis induced by staurosporine, camptothecin, and/or dexamethasone as described herein. See, e.g., FIGS. 1-21.

The invention will be further described in the following examples, which do not limit the scope of the invention described in the claims.

EXAMPLES

Example 1—Kallikrein 6 Polypeptides Promote Resistance of Lymphocytes to Apoptosis Model Systems The effect of KLK6 polypeptides on immune cell survival was examined using whole splenocyte populations derived from C57BL6/J or PAR1 deficient mice or using the Jurkat T-leukemic cell line (clone E6-1, TIB-152 American Type Culture Collection). Eight to 12 week old C57 mice were obtained from Jackson Laboratories. Mice deficient in PAR1$^{-/-}$ (B6.129S4-F2r$^{tm1Ajc}$/J) were also obtained from Jackson and backcrossed to C57BL6/J for 10 generations such that C57 mice served as wild type controls in each experiment.

Cell Culture

Spleens were homogenized in RPMI-1640, red blood cells lysed with ammonium chloride buffer, and splenocytes cultured in tissue culture treated 96 well plates at a density of 7.5×10$^5$ cells/mL. All experiments were performed in serum free X-Vivo media (Lonza, Mapleton, Ill.) containing 2 mM Glutamax, 1 mM sodium pyruvate, 50 U/mL penicillin-streptomycin, 10 mM HEPES, 50 µM 2-β-mercaptoethanol, and 10 µM non-essential amino acids (Invitrogen). Jurkat T cells were maintained in log-phase growth in the same defined media. The cells were maintained at 37° C. in 95% air and 5% CO2. The culture conditions were examined in triplicate within a given experiment, and all experiments repeated at least twice.

Reagents

Recombinant KLK1 polypeptides and KLK6 polypeptides were expressed using a baculovirus/insect system, purified and activated as described elsewhere (Bernett et al., J. Biol. Chem., 277:24562-24570 (2002); and Laxmikanthan et al., Proteins, 58:802-814 (2005)). Thrombin derived from bovine serum was obtained from Sigma (St. Louis, Mo.) and used at 50 nM. PAR1, PAR2 and PAR4-activating polypeptides (-APs) were obtained from Peptides International (Louisville, Ky.). Recombinant KLK polypeptides were used at concentrations ranging from 1 to 10 µg/mL (40 to 400 nM), and PAR-APs were used at 100 µM, concentrations shown elsewhere to induce intracellular signaling (Vandell et al., J. Neurochem., 107:855-870 (2008)). The concentrations of KLK6 polypeptides examined encompass the physiologic level seen in normal cerebrospinal fluid (0.5-2 µg/mL) (Diamandis et al., Clin. Biochem., 33:579-583 (2000); Zarghooni et al., Clinical Biochemistry, 35:225-231 (2002); and Borgono et al., Mol. Cancer Res., 2:257-280 (2004)) and 5-fold excess which models elevated levels seen at sites of CNS inflammation in MS and its animal models (Scarisbrick et al., Brain, 125:1283-1296 (2002); Christophi et al., J. Neurochem., 91:1439-1449 (2004); Scarisbrick et al., J. Neuroimmunology, 178:167-176 (2006); Scarisbrick et al., Biol. Chem., 389:739-745 (2008)).

To delineate the scope of action of KLK6 polypeptides on immune cell survival, its effects on cell survival were examined in several different cell death paradigms encompassing both the intrinsic and extrinsic cell death pathways. First, spontaneous cell death, which is known to occur after harvest and plating of splenocytes in vitro and which is referred to as resting cell death, was examined. In addition, cell death was induced using the topoisomerase inhibitor camptothecin (1.0 µM), the mitogen concanavalin A (ConA, 5 µg/mL), or a combination of ConA and camptothecin. Fas ligand cell death was induced using Fas Ligand/TNFSF6 (2 µg/mL) cross linked with anti-polyHistidine (10 µg/mL). Cell death due to stimulation by the glucocorticoid Dexamethasone (0.1 µM) and by the protein kinase inhibitor staurosporine (1 µM) were also examined. All agents to induce cell death were obtained from Sigma and were either applied to cultures at the time of cell plating simultaneously with KLK6 polypeptides, or after cultures had first been pre-incubated with KLK6 polypeptides for 2 hours.

Flow Cytometry

Following experimental incubation periods, which ranged from 4 to 72 hours, cells were harvested and stained with combinations of antibodies recognizing to CD45, CD3, B220, or the early apoptotic marker Annexin-V, conjugated to FITC, PE, or APC (e-Bioscience, San Diego, Calif.). In each case, either propidium iodide (PI) or 7-AAD were used to label dead cells (Sigma). Cells were analyzed by flow cytometry using a FACSCalibur flow cytometer (BD Biosciences, Mountain View, Calif.). Live immune cells were defined as those which were positive for the common leukocyte antigen CD45, but negative for PI. Early and late apoptotic/dead cells were distinguished using a combination of AnnexinV-PE and 7-AAD or AnnexnV-FITC and PI (BD Biosciences). FlowJo software (Ashland, Oreg.) was used to quantify different cell populations in flow cytometry experiments. Potential effects on cell proliferation were examined by labeling cells with carboxyfluorescein succinimidyl ester (CFSE, Invitrogen, Carlsbad, Calif.) prior to plating followed by analysis using the FlowJo proliferation platform at the completion of each experiment.

To compare multiple cell culture conditions within a given experiment, the mean and standard error across experimental groups were analyzed by One-Way Analysis of Variance followed by Student-Newman-Keuls (SNK) post hoc test except when data were not normally distributed when ANOVA on Ranks and Mann-Whitney-U analyses were performed. Statistical differences between two groups were compared using the Student's t-test or the Rank Sum test when data were non-linear. $P<0.05$ was considered statistically significant.

Western Blot Analysis

Protein lysates were separated on SDS-polyacrylaminde gels prior to transfer to nitrocellulose membranes. Antibodies to detect Bcl-XL (B-cell lymphoma-extra large) and Bim (Bcl-2-interacting mediator of cell death) polypeptides were obtained from Cell Signaling Technology (Danvers, Mass.). The PARP antibody was obtained from Dr. S. Kauffman (Eischen et al., Blood, 90:935-943 (1997)). Equal loading was verified by re-probing blots for β-Actin (Novus, Littleton, Colo.). In all cases, polypeptides of interest were detected using chemiluminescence (Pierce, Rockford, Ill.). All Western blots were repeated at least three times using separate cell culture preparations with similar results.

Differential Effects of KLK1 and KLK6 Polypeptides on Immune cell Proliferation and Survival As a first approach to define the possible immunological actions of KLK6 polypeptides, its effects on proliferation and survival of murine splenocytes were examined and compared to another kallikrein family member, KLK1. While KLK6 polypeptides did not significantly alter splenocyte proliferation after 24 or 72 hours, KLK6 polypeptides promoted a substantial and dose dependent reduction in the number of cells positive for markers of cell death across the same time points (FIGS. 1A-D, see also FIGS. 4A-D, 5A-C, 6A-B, 7A-D, 9A-B, and 11A-D). KLK6 polypeptides significantly reduced cell death under resting conditions when pulsed at either 1 or 10 µg/mL at the time of plating. Ten µg/mL of KLK6 polypeptides generated significantly better rescue than 1 µg/mL (FIG. 1B) and therefore all subsequent experiments were performed using the higher concentration. Also, KLK6 polypeptides promoted cell survival at both 24- and 72-hour time points such that most subsequent experiments were carried out to 24 hours. Parallel examination of a second kallikrein, KLK1, produced in an identical fashion to KLK6 (Laxmikanthan et al., Proteins, 58:802-814 (2005)), did not significantly impact cell survival. KLK1 polypeptides however promoted a significant increase in the percent of divided cells when pulsed with 10 µg/mL and examined at 24 hours post-stimulation. Significant differences in proliferation were not seen at lower concentrations of KLK1, or when cells were examined 72 hours post-exposure. KLK6 polypeptides did not produce similar robust effects on cell proliferation at any of the concentrations or time points examined indicating proliferative effects are unlikely to account for its ability to increase the number of viable cells.

KLK6 Polypeptides Protect T Cells and B Cells Across Multiple Cell Death Paradigms To determine how robust the survival promoting effects of KLK6 polypeptides are, the ability of KLK6 polypeptides to prevent cell death across a range of paradigms was examined. KLK6 polypeptides not only prevented the death of splenocytes that occurred after explant and culture (FIGS. 1A-D, 4A-D, 5A-C, 6A-B, and 7A-D), but also that seen in response to 0.1 µM dexamethasone (FIGS. 4A-D, 5A-C, 6A-B, and 7A-D), in the presence of graded concentrations of Fas ligand (FIGS. 4A-D), and after exposure to 1 µM staurosporine (FIGS. 6A-B). KLK6 polypeptides also blocked the death of Jurkat T cells under resting conditions and when exposed to 1 µM camptothecin, 1 µM camptothecin plus 5 µg/mL ConA, or Fas ligand receptor cross linking (FIGS. 4A-D and 11A-D). Co-labeling splenocytes with markers for T or B cell subsets in addition to markers for cell death demonstrated that KLK6-rescue effects occurred across both populations (FIGS. 4A-D and 7A-D). The ability of KLK6 polypeptides to rescue splenocytes or Jurkat cells across cell death paradigms was consistently observed when KLK6 polypeptides were applied simultaneously with death inducing agents. A two hour pre-incubation with KLK6 polypeptides prior to dexamethasone application was shown to result in a small but statistically significant enhancement of survival (FIGS. 4A-D, P<0.05).

Additional results include using ATP and cisplatin with murine T and B lymphocytes to demonstrate that recombinant KLK6 blocks apoptosis. KLK6 protected immune cells from cellular injury and death even in the face of a strong apoptosis inducing agent (ATP) or a strong chemotherapeutic agent (Cisplatin) (FIGS. 2A-C and 3A-C).

As Little as a 5-Minute Exposure to KLK6 Polypeptides was Sufficient to Promote Robust Survival To determine whether prolonged or continual exposure to KLK6 polypeptides was necessary to promote significant rescue effects, the potential pro-survival effects of abbreviated periods of KLK6 polypeptide-stimulation were examined (FIGS. 5A-C). Under both resting conditions and in the presence of dexamethasone, as little as a 5-minute pulse with KLK6 polypeptides was sufficient to reduce cell death significantly when cells were subsequently cultured for an additional 24 hours in the absence of KLK6 polypeptides. In the presence of dexamethasone for 24 hours, significant rescue effects were also seen with 5-, 30-, or 60-minute pulses of KLK6 polypeptides, and the magnitude of rescue did not differ significantly from that seen with continual KLK6 polypeptide exposure over the full period of dexamethasone treatment. Experimental endpoints under resting conditions were also extended to 48 hours, and in this case, while continual KLK6 polypeptide stimulation promoted robust survival, KLK6 polypeptide pulses up to 60 minutes in length were insufficient to induce significant rescue.

KLK6 Polypeptides Halt the Apoptotic Cascade

The ability of KLK6 polypeptides to specifically affect apoptosis in splenocytes and Jurkat cells was assessed by comparing KLK6 polypeptide-induced changes in the relative number of live cells (AnnexinV−, PI−), early apoptotic cells (AnnexinV+, PI−), and dead cells (AnnexinV+, PI+) across several cell death paradigms (FIGS. 6A-B and 11A-D). In some cases, 7-AAD was used in place of PI.

In the case of Jurkat T cells under resting conditions, KLK6 polypeptides promoted a reduction in the number of dead cells and a corresponding increase in the number of live cells, but did not significantly alter the number of early apoptotic cells when examined at 4, 24, or 48 hours post plating (FIGS. 11A-D). When Jurkat cells were challenged with the topoisomerase inhibitor camptothecin, with ConA, or a combination of these agents, KLK6 polypeptides reduced the number of dead cells at the 4-, 24-, and 48-hour time points examined, mirroring observations under resting conditions. A significant increase in the number of live cells was also seen in each circumstance except after 48-hour exposure to the Camptothecin or the ConA+Camptothecin combination. Jurkat cells cultured in the presence of KLK6 in addition to ConA, or ConA plus camptothecin, showed an accumulation of cells at early apoptotic stages at the 24-hour time point examined. By 48 hours, the significant increase in early apoptotic cells induced by the presence of KLK6 polypeptides was seen under all three death-inducing conditions, including camptothecin alone.

In addition, over expression of KLK6 polypeptides in the Jurkat leukemia T cell line promoted the resistance of these cells to apoptosis under resting conditions or in the presence of staurosporine (FIGS. 12A-B).

Examination of live, early apoptotic, and dead cells in murine splenocyte cultures generated results parallel to those observed in Jurkat cells. That is, KLK6 polypeptides reduced overall cell death by increasing the number of cells in the live and/or early apoptotic populations depending on the conditions examined (FIG. 6A). Under resting conditions over 24 hours, the presence of KLK6 polypeptides significantly reduced the number of dead cells with a corresponding increase in the live population, while the number of early apoptotic cells was largely unchanged. In the presence of dexamethasone (0.1 µM) or staurosporine (1 µM), co-exposure to KLK6 polypeptides promoted the expected significant decrease in the number of dead cells and a small but significant increase in the live cell population. In addition, under these death-inducing conditions, KLK6 polypeptides also promoted a substantial and significant increase in the number of early apoptotic cells.

The ability of KLK6 polypeptides to block apoptosis was further assessed by examining the effects of KLK6 polypeptides on cleavage of poly-ADP ribose polymerase (PARP), one of the final caspase substrates cleaved in the apoptotic cascade (FIG. 6B). Significant levels of cleaved PARP were detected in splenocytes grown under resting conditions and when exposed to camptothecin for 24 hours. In each case, co-exposure to KLK6 polypeptides significantly reduced the amount of cleaved PARP detected.

KLK6 Polypeptide-Mediated Lymphocyte Survival Depends in Part on Activation of PAR1

To investigate the potential involvement of PAR1 polypeptides in KLK6 polypeptide-mediated lymphocyte rescue, the impact of PAR1 polypeptide deficiency was determined using splenocytes isolated from PAR1 knockout mice. Additionally, the effects of KLK6 polypeptides were compared to commercially available short synthetic PAR-derived peptide sequences that selectively activate PAR1, 2, or 4 (PAR-APs) (FIGS. 7A-D). In the case of CD3+ T cells, the absence of PAR1 severely impaired the ability of KLK6 polypeptides to rescue cells under resting conditions but any effect in the presence of dexamethasone was not statistically significant (FIG. 7A). PAR1 deficiency also blocked the ability of KLK6 polypeptides to rescue B220+ B cells from cell death under resting conditions and reduced KLK6 polypeptide-mediated rescue in the presence of dexamethasone (FIG.

7B). While these results indicate that KLK6 polypeptide-mediated lymphocyte rescue is dependent at least in part on the presence of PAR1, activation of PAR1 or PAR2 alone using PAR-APs, or in combination with each other (not shown), or in combination with PAR4-AP, were not sufficient to recapitulate the rescue effects seen with KLK6 polypeptides (FIGS. 7C and 7D). Indeed, in the presence of dexamethasone, PAR1-AP enhanced the magnitude of cell death observed (FIG. 7C).

KLK6 Polypeptides Differentially Regulate Bcl-2 Family Member Signaling in a PAR1-Dependent Fashion In murine lymphocytes, deletion of protease activated receptor 2 (PAR2) (FIG. 8), like PAR1 (FIGS. 7A-D), diminished the ability of KLK6 to promote cell survival in resting cells and those treated with the corticosteroid dexamethasone. Thus, targeting PAR1 and/or PAR2 is another potential mechanism to target (i.e., increase or decrease) the activity of KLK6.

To further delineate the mechanism by which KLK6 polypeptides prevent cell death, effects on pro- and anti-apoptotic signaling pathways were examined. When splenocytes were exposed to either camptothecin or ConA in the presence of KLK6 polypeptides, significant elevations in the pro-survival protein Bcl-XL were observed (FIGS. 9A-B). As a corollary, under resting conditions, or in the presence of camptothecin, or ConA, KLK6 polypeptides promoted significant reductions in the pro-apoptotic protein Bim. The ability of KLK6 polypeptides to alter these signaling cascades was largely blocked in mice deficient in PAR1.

Example 2—KLK6 Polypeptides Promote the Survival of T Cells, Monocytes, and B Cells Murine T cells (CD3+), monocytes (CD11b+), and B cells (B220+) each undergo cell death when harvested from the mouse spleen and grown in culture for 24 hours. When exposed to 10 μg/mL of recombinant KLK6 polypeptides at the time of plating, a significant reduction in the amount of cell death was observed (FIG. 10; P<0.05, ANOVA, SNK post hoc test). Cell death was measured by flow cytometric analysis of PI labeling.

Example 3—KLK6 Polypeptides Promote the Survival of Oligodendrocytes

KLK6 polypeptides promoted the survival of murine oligodendrocytes in a dose dependent fashion. The protein tyrosine kinase inhibitor, staurosporine (0.5 μM), was shown to promote death of the Oli Neu oligodendrocyte cell line after an 18 hour exposure period. Cell death was detected by PI labeling and quantitatively analyzed by flow cytometry. When cells were pre-exposed to 5 or 10 μg/mL of recombinant KLK6 polypeptides prior to stuarosporine exposure, a significant reduction in the amount of cell death was observed (FIG. 13; P<0.001, One Way ANOVA, SNK post hoc test).

Example 4—KLK6 Polypeptides Promote the Survival of Glioma Cells

KLK6 polypeptides promoted the survival of human glioma cells. The U251 human glioblastoma cell line was grown under control conditions or in the presence of the protein kinase inhibitor staurosporine (1 μM), which induced a considerable increase in cell death. Cell death was measured by flow cytometric detection of propidium iodide labeling. When glioma cells were pre-exposed to KLK6 polypeptides for 2 hours prior to application of staurosporine, a significant decrease in cell death was observed (FIG. 14; P<0.005, One Way ANOVA, SNK post hoc test).

In other assays, recombinant KLK6 was demonstrated to reduce death of a glioblastoma multiforme cell line, U251, in a dose dependent fashion in the presence of the tyrosine kinase inhibitor staurosporine (FIGS. 15A-B). Annexin V labeling in combination with propidium iodide (PI) was used to demonstrate that recombinant KLK6 not only reduced the number of dead GBM cells, but also the number of apoptotic cells while simultaneously increasing the number of live cells (FIGS. 16A-C).

Figure 21:
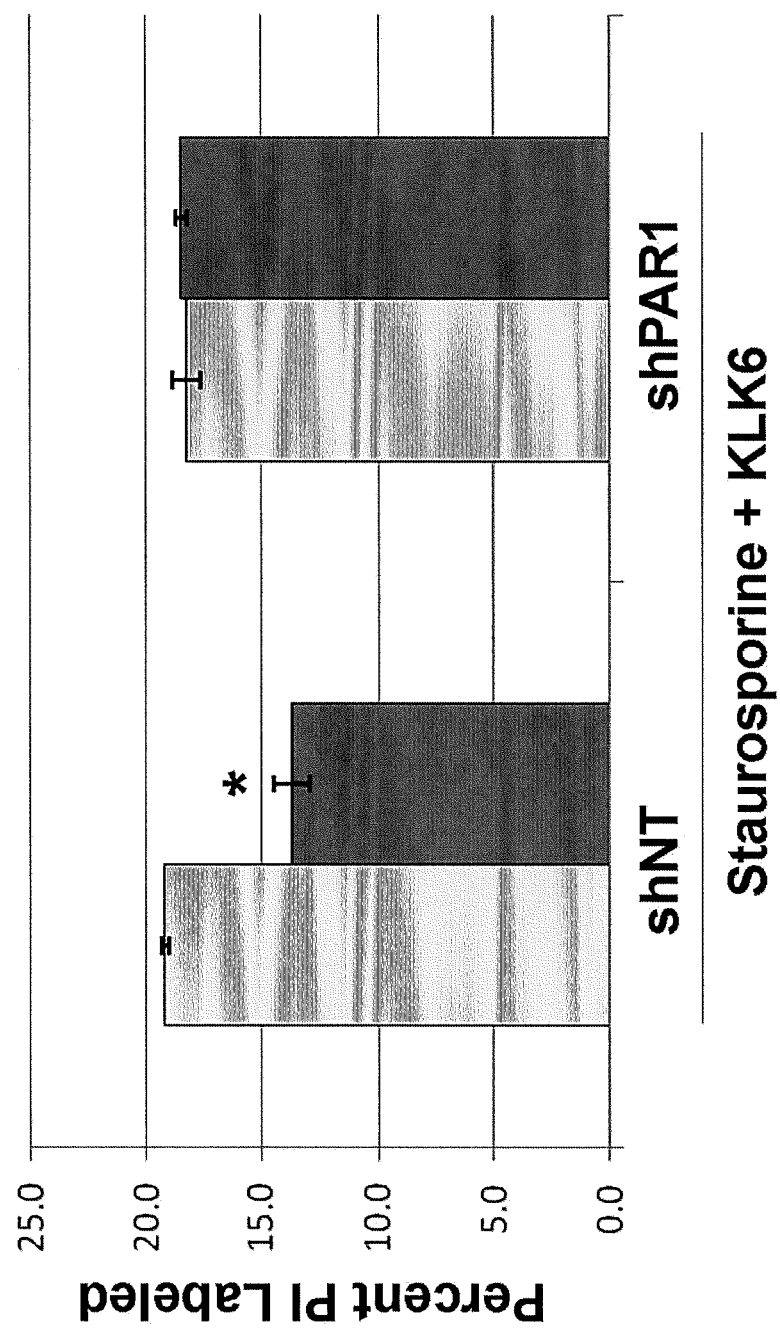
FIG. 21 contains results demonstrating that knock down of PAR1 in U251 GBM cells diminishes the ability of KLK6 to promote resistance to staurosporine induced cell death. U251 GBM cells were stably transfected with a vector containing a PAR1-specific small interfering RNA expressed from a short hairpin RNA (shPAR1) or with a no template control vector (shNT). Recombinant KLK6 was not able to significantly reduce staurosporine induced apoptosis in shPAR1 expressing U251 cells, although significant rescue was preserved in those cells expressing the no template control vector alone (*P<0.05, Students t-test).

In addition, KLK6 polypeptide over expression promoted the resistance of U251 GBM cells to staurosporine induced cell death (FIGS. 17A-C) as well as to radiation (RT) and temozolomide (TMZ) alone, or in combination (FIGS. 18A-B and 19A-B). RT plus TMZ is a current standard of care for GBM patients, and targeting KLK6 may therefore sensitize these tumor cells to conventional therapies, thereby improving patient survival. These findings were demonstrated using a KLK6 over expression construct and clonogenicity assays (FIGS. 18A-B and 19A-B). Recombinant KLK6, or KLK6 polypeptide over expression, also promoted resistance of U251 GBM cells to the chemotherapeutic, cisplatin (FIGS. 20A-B). In GBM U251 cells, down regulation of PAR1 using a PAR1 targeting small hairpin vector blocked the ability of KLK6 to promote resistance to cell death induced by staurosporine. Thus, targeting PAR1 is another method to target the ability of KLK6 to alter cell survival in GBM (FIG. 21).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the susceptibility of cancer cells to apoptosis, wherein said cancer cells are present within a mammal and have Kallikrein 6 (KLK6) polypeptide-induced resistance to apoptosis, wherein said method comprises:
   administering an inhibitor of KLK6 polypeptide activity to said mammal under conditions wherein said inhibitor reduces the level of KLK6 polypeptide-induced resistance to apoptosis triggered by an apoptosis-inducing agent of said cancer cells within said mammal, wherein said inhibitor is an anti-KLK6 antibody.

2. The method of claim 1, wherein said mammal is a human.

3. The method of claim 1, wherein said method further comprises administering an anti-cancer agent to said mammal.

4. The method of claim 3, wherein said anti-cancer agent is temazolamide, avastin, taxol, or radiation.

* * * * *

UNITED STATES PATENT AND TRADEMARK OFFICE
CERTIFICATE OF CORRECTION

PATENT NO. : 9,669,094 B2  
APPLICATION NO. : 13/962686  
DATED : June 6, 2017  
INVENTOR(S) : Isobel A. Scarisbrick Page 1 of 1

It is certified that error appears in the above-identified patent and that said Letters Patent is hereby corrected as shown below:

On the Title Page

Column 2 (Other Publications), please delete "beween" and insert -- between --, therefor;

In the Claims

Column 27, Line 16 (Claim 3), before "anti-cancer" insert -- additional --, thereof;

Column 27, Line 18 (Claim 4), before "anti-cancer" insert -- additional --, thereof;

Column 27, Line 19 (Claim 4), please delete "temazolamide," and insert -- temozolomide, --, therefor.

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*